(12) United States Patent
Hayes et al.

(10) Patent No.: US 12,115,113 B2
(45) Date of Patent: Oct. 15, 2024

(54) PATIENT SUPPORT APPARATUS COMMUNICATION SYSTEMS

(71) Applicant: Stryker Corporation, Kalamazoo, MI (US)

(72) Inventors: Michael Joseph Hayes, Kalamazoo, MI (US); Aaron Douglas Furman, Kalamazoo, MI (US); Christopher John Hopper, Kalamazoo, MI (US); John P. Geer, Ann Arbor, MI (US); Joshua Elmer Mix, Portage, MI (US); David Terrance Becker, Grand Rapids, MI (US); Jonathan Mark Greenbank, Plainwell, MI (US)

(73) Assignee: Stryker Corporation, Portage, MI (US)

( * ) Notice: Subject to any disclaimer, the term of this patent is extended or adjusted under 35 U.S.C. 154(b) by 966 days.

(21) Appl. No.: 17/131,986

(22) Filed: Dec. 23, 2020

(65) Prior Publication Data

US 2021/0106476 A1     Apr. 15, 2021

Related U.S. Application Data

(63) Continuation of application No. 15/909,131, filed on Mar. 1, 2018, now Pat. No. 10,898,398, which is a
(Continued)

(51) Int. Cl.
*A61G 7/018*     (2006.01)
*G16H 40/20*     (2018.01)

(52) U.S. Cl.
CPC ............. *A61G 7/018* (2013.01); *G16H 40/20* (2018.01); *A61G 2203/46* (2013.01)

(58) Field of Classification Search
CPC ..... A61G 7/018; A61G 2203/46; G16H 40/20
See application file for complete search history.

(56) References Cited

U.S. PATENT DOCUMENTS 5,699,038 A * 12/1997 Ulrich .................... G16H 40/20
340/286.07
5,781,442 A * 7/1998 Engleson ............... G16H 40/20
700/214
(Continued)

FOREIGN PATENT DOCUMENTS

WO    WO-2009055635 A1 *  4/2009  ............. A61B 5/002

*Primary Examiner* — Eric J Kurilla
(74) *Attorney, Agent, or Firm* — Warner Norcross + Judd LLP

(57) ABSTRACT

Patient support apparatuses, such as beds, cots, stretchers, recliners, operating tables, and the like include wireless mesh network transceivers that enable them to communicate with each other, and other devices, via mesh networks and/or ad hoc networks. One or more additional wireless transceivers are included, such as WiFi transceivers that enable direct communication with a healthcare facility network, such as an Ethernet. The mesh network communication between patient support apparatuses and other devices is used for any one or more of: extending the communication range of the existing IT infrastructure, efficiently routing data to the healthcare facility network, determining location of the patient support apparatuses and devices, transporting patient data from one patient support to the next as the patient moves, and for other aspects.

14 Claims, 10 Drawing Sheets

Related U.S. Application Data continuation of application No. 13/802,855, filed on Mar. 14, 2013, now Pat. No. 9,937,090, which is a continuation-in-part of application No. 13/680,699, filed on Nov. 19, 2012, now Pat. No. 8,674,826, which is a continuation of application No. 13/356,204, filed on Jan. 23, 2012, now Pat. No. 8,319,633, which is a continuation of application No. 12/573,545, filed on Oct. 5, 2009, now Pat. No. 8,102,254, which is a continuation of application No. 11/277,838, filed on Mar. 29, 2006, now Pat. No. 7,598,853.

(60) Provisional application No. 61/640,138, filed on Apr. 30, 2012, provisional application No. 60/734,083, filed on Nov. 7, 2005, provisional application No. 60/665,955, filed on Mar. 29, 2005.

(56) References Cited

U.S. PATENT DOCUMENTS

| | | | | |
|---|---|---|---|---|
| 6,147,592 | A * | 11/2000 | Ulrich | G08B 25/12 340/286.07 |
| 6,160,478 | A * | 12/2000 | Jacobsen | A61B 5/6838 128/903 |
| 6,344,794 | B1 * | 2/2002 | Ulrich | G06K 17/0022 340/8.1 |
| 6,970,097 | B2 * | 11/2005 | Welles, II | G01S 1/725 340/8.1 |
| 7,319,386 | B2 * | 1/2008 | Collins, Jr. | A61G 7/0527 340/286.07 |
| 7,598,853 | B2 * | 10/2009 | Becker | G08B 13/14 340/539.11 |
| 8,082,160 | B2 * | 12/2011 | Collins, Jr. | H04L 69/18 600/300 |
| 8,334,777 | B2 * | 12/2012 | Wilson | G16H 40/20 340/286.07 |
| 10,335,334 | B2 * | 7/2019 | Seim | A61G 7/0524 |
| 2002/0014951 | A1 * | 2/2002 | Kramer | G16H 10/60 340/286.07 |
| 2002/0183979 | A1 * | 12/2002 | Wildman | G07C 9/28 702/188 |
| 2003/0160698 | A1 * | 8/2003 | Andreasson | G16H 20/13 705/3 |
| 2005/0035862 | A1 * | 2/2005 | Wildman | G08B 21/0446 340/572.1 |
| 2006/0058587 | A1 * | 3/2006 | Heimbrock | A61G 7/0507 600/300 |
| 2006/0279427 | A1 * | 12/2006 | Becker | G16H 40/67 340/539.13 |
| 2007/0094045 | A1 * | 4/2007 | Cobbs | G16H 40/20 705/2 |
| 2007/0210917 | A1 * | 9/2007 | Collins, Jr. | G08B 5/222 340/539.1 |
| 2008/0001763 | A1 * | 1/2008 | Raja | G08B 21/245 340/572.1 |
| 2008/0205311 | A1 * | 8/2008 | Perkins | A61B 5/1113 370/310 |
| 2008/0242944 | A1 * | 10/2008 | Sharma | G16H 10/65 600/300 |
| 2009/0058635 | A1 * | 3/2009 | LaLonde | H04W 12/50 340/539.11 |
| 2009/0102612 | A1 * | 4/2009 | Dalbow | G16H 10/60 340/10.4 |
| 2009/0112630 | A1 * | 4/2009 | Collins, Jr. | H04L 67/125 705/2 |
| 2009/0119843 | A1 * | 5/2009 | Rodgers | G16Z 99/00 705/3 |
| 2009/0214009 | A1 * | 8/2009 | Schuman, Sr. | H04L 67/52 379/106.02 |
| 2010/0117823 | A1 * | 5/2010 | Wholtjen | G01S 11/16 340/539.13 |
| 2010/0145723 | A1 * | 6/2010 | Hudson | G06Q 40/00 342/357.31 |
| 2010/0245092 | A1 * | 9/2010 | Albert | A61G 7/018 340/573.7 |
| 2011/0208541 | A1 * | 8/2011 | Wilson | A61G 7/0527 705/2 |
| 2011/0210925 | A1 * | 9/2011 | Pittenger | G16H 40/67 715/761 |
| 2011/0247139 | A1 * | 10/2011 | Tallent | A61G 7/018 5/613 |
| 2014/0026322 | A1 * | 1/2014 | Bell | G16H 40/63 715/738 |
| 2014/0184409 | A1 * | 7/2014 | Vanderpohl, III | G08B 21/18 340/539.22 |

\* cited by examiner

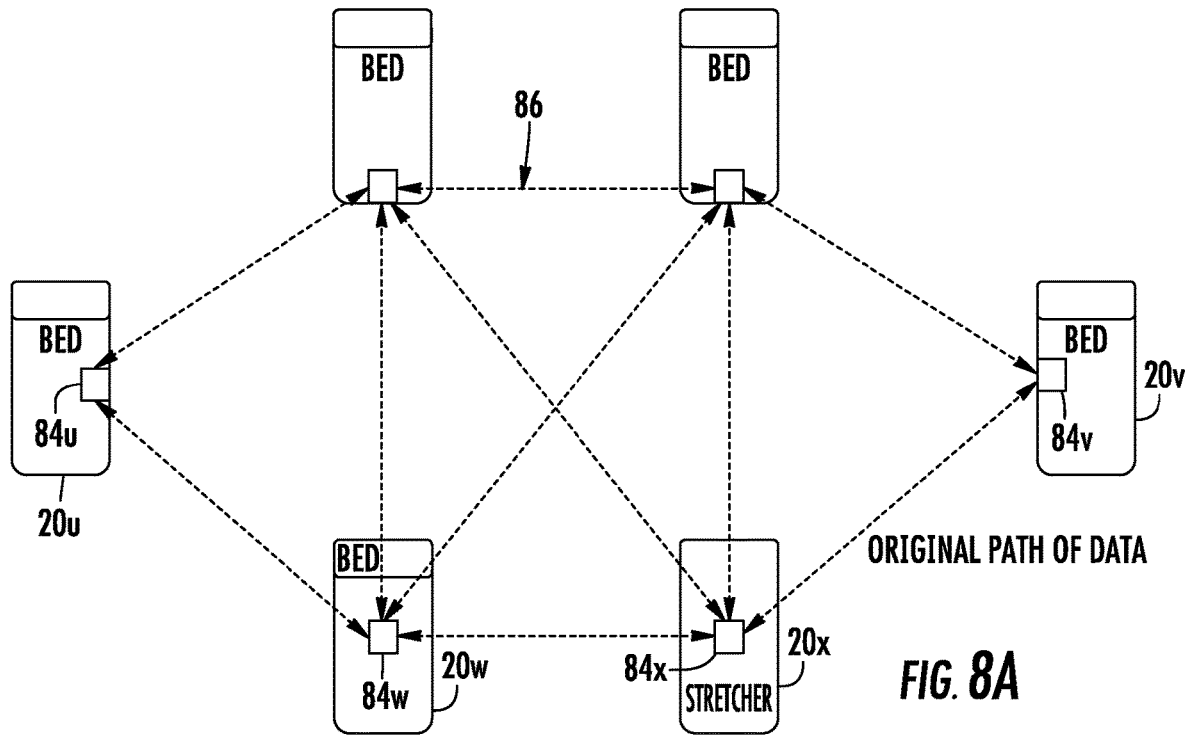
FIG. 8A ORIGINAL PATH OF DATA
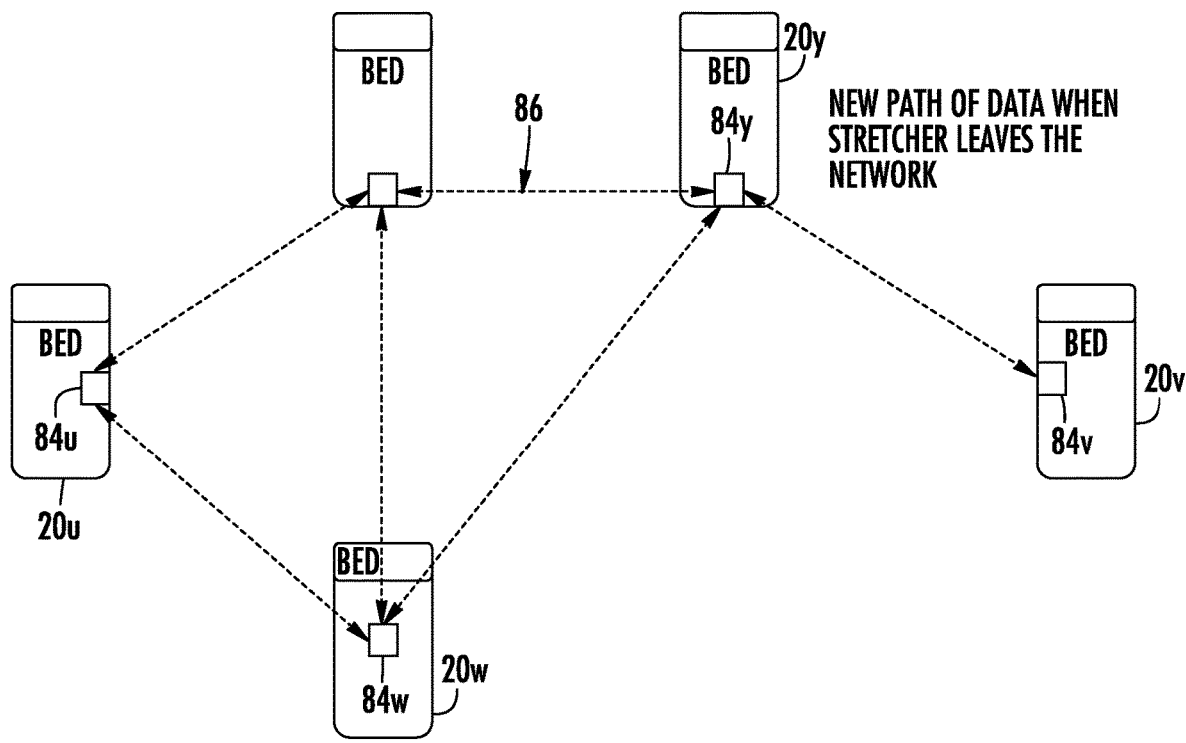
FIG. 8B NEW PATH OF DATA WHEN STRETCHER LEAVES THE NETWORK

PATIENT SUPPORT APPARATUS COMMUNICATION SYSTEMS

CROSS-REFERENCE TO RELATED APPLICATIONS

This application claims priority to U.S. patent application Ser. No. 15/909,131 by inventors Michael Hayes et al. and entitled PATIENT SUPPORT APPARATUS COMMUNICATION SYSTEMS, which in turn claims priority to U.S. patent application Ser. No. 13/802,855 filed Mar. 14, 2013 by inventors Michael Joseph Hayes et al, and entitled PATIENT SUPPORT APPARATUS COMMUNICATION SYSTEMS, which claims benefit of U.S. provisional patent application Ser. No. 61/640,138 filed Apr. 30, 2012 by applicants Michael Hayes et al. and entitled PATIENT SUPPORT APPARATUS COMMUNICATION SYSTEMS and which is also a Continuation-in-Part of U.S. patent application Ser. No. 13/680,699 filed Nov. 19, 2012, now U.S. Pat. No. 8,674,826, which is a continuation of U.S. patent application Ser. No. 13/356,204 filed Jan. 23, 2012, now U.S. Pat. No. 8,319,633, which is a continuation of U.S. patent application Ser. No. 12/573,545 filed Oct. 5, 2009, now U.S. Pat. No. 8,102,254, which is a continuation of U.S. patent application Ser. No. 11/277,838 filed Mar. 29, 2006, now U.S. Pat. No. 7,598,853, which claims benefit of U.S. provisional patent application Ser. No. 60/665,955 filed Mar. 29, 2005 and claims benefit of U.S. provisional patent application Ser. No. 60/734,083 filed Nov. 7, 2005, the complete disclosures of which are hereby incorporated herein by reference.

BACKGROUND OF THE INVENTION

The present invention relates to patient support apparatuses, such as cots, stretchers, beds, recliners, operating tables, and other structures used to support patients in a healthcare environment. More particularly, the present invention relates to systems and methods by which the patient support apparatuses may communicate with each other and with other structures for one or more purposes.

In a healthcare setting, it is often desirable for information about a patient support apparatus to be forwarded from the patient support apparatus to a one or more remote locations, such as a nurses' station, where caregivers can review such information without the need to physically travel to each and every room in the healthcare environment (e.g. a hospital, medical center, long term care facility, or the like). Often such information is forwarded to a healthcare computer network, such as an Ethernet, where one or more servers make the information available for display on any one or more computers or mobile devices that are communicatively coupled to the healthcare computer network.

In some instances, the patient support apparatuses forward such information via a direct wireless connection to one or more wireless access points of the healthcare network. Such information may be forwarded via IEEE 802.11 standards. In other situations, such information may be forwarded via a wired connection to the healthcare network. Regardless of the manner in which the patient support apparatus is forwarded to the healthcare network, it is desirable for the patient support apparatus information to include data that either identifies the location of the patient support apparatus, or that allows a computer—such as, but not limited to, a server on the network—to determine the location of the patient support apparatus. Such information allows caregivers to know where in the healthcare facility the patient support apparatus is located. In this manner, if any of the information requires action on the part of the caregiver, the caregiver knows where to go to take the proper action.

SUMMARY OF THE INVENTION

The present invention provides systems and methods for determining the location of patient support apparatuses, as well as systems and methods that improve the communications ability of the patient support apparatuses. Such improved communications may be with a healthcare computer network, and/or such improved communications may be between the patient support apparatuses themselves. In still other embodiments, such improved communications may be with medical devices positioned within a vicinity of the patient support apparatus. In some embodiments, the improved communication may expand the communication range of a healthcare computer network without being dependent upon the healthcare facility's infrastructure to transmit data from device to device The improved communication relates to either or both of the content of the information communicated, as well as the quality of the reception and transmission of the electromagnetic signals that carry the information. In some embodiments, patient information is communicated between patient support apparatuses during the transfer of a patient from one support apparatus to another, thereby allowing the patient information to follow the patient in whatever patient support apparatus he or she is positioned on. In other embodiments, the location of a patient support apparatus is determined by triangulation with signals received from other patient support apparatuses. In still other embodiments, a mesh network is created between patient support apparatuses for communicating information from the support apparatuses to the healthcare network. Such information includes information about the status of various features of the patient support information, and/or it includes information about medical devices positioned near to the patient support apparatuses, and/or it includes patient information.

According to one embodiment, a patient support apparatus is provided that includes a base, a frame supported by the base, a patient support deck, and a control system. The patient support deck is supported by the frame and adapted to provide support for a patient. The control system controls a feature of the patient support apparatus and includes first and second transceivers. The control system is further adapted to be able to wirelessly receive information via the first transceiver from a different patient support apparatus about a feature of the different patient support apparatus, and the control system is further adapted to be able to forward the information off of the patient support apparatus via the second transceiver.

In other aspects, the first transceiver operates in accordance with an Institute of Electrical and Electronics Engineers (IEEE) 802.15.4 standard, and the second transceiver operates in accordance with an IEEE 802.11 standard, although other communication protocols may be used for both transceivers. The transmitted information includes information identifying the different patient support apparatus and information identifying a location of the different patient support apparatus. The control system is further adapted to be able to forward the information off of the patient support apparatus via the first transceiver, wherein the control system chooses between the first and second transceivers for forwarding the information off of the patient support apparatus. Such a choice may be made based at least partially upon assessing signal strengths of the first and second transceivers with potential recipients of the information.

The control system is adapted to process location information received via the first transceiver from the different patient support apparatus and use the location information in order to generate an estimate of a location of the patient support apparatus. The estimate of location may be based at least partially upon a signal strength of the location information received via the first transceiver from the different patient support apparatus. Alternatively, the estimate of location may be based upon location information received via the first transceiver from a plurality of different patient support apparatuses.

A memory positioned on the patient support apparatus is adapted to store data about a patient currently supported on the patient support apparatus, and the control system is adapted to wirelessly transmit the patient data to another patient support apparatus when the patient is transferred to the another patient support apparatus. The patient support apparatus is able to wirelessly transmit the patient data to the another patient support apparatus in response to a caregiver manually manipulating a control on the patient support apparatus. The patient support apparatus also includes a visual display adapted to provide a visual indication when the patient data has been successfully transmitted to the another patient support apparatus. The control system is also adapted to clear the patient data from the memory when a caregiver manually manipulates a control on the patient support apparatus, or when some other indicator provides an indication that patient transfer is complete.

The patient support apparatus is also configurable such that the first transceiver is able to receive medical device data from a medical device, and the control system can forward the medical device data off of the patient support apparatus via the second transceiver. In other embodiments, the control system is configured to forward the medical device data off of the patient support apparatus via the first transceiver as well, and the control system chooses between the first and second transceivers for forwarding the information off of the patient support apparatus. The medical device may include one or more of the following: a ventilator, a vital signs monitor, a respirator, an infusion pump, an IV pump, a temperature sensor, a temperature management device, and a blood oxygen saturation monitor.

The first transceiver may be configured to transmit network data to a medical device, wherein the network data is received by the patient support apparatus from a healthcare network. The patient support apparatus may receive the network data either from the first or the second transceivers.

An RF transceiver may be included on the patient support apparatus that is adapted to read patient information from an RF identification (ID) tag worn by a patient positioned on the patient support apparatus. The control system associates the patient information with a unique identifier of the patient support apparatus and forward both the patient information and the unique identifier to a healthcare network.

The control system may be configured to choose another patient support apparatus to which the information is forwarded via the first transceiver. This choice may be dynamically updated based at least partially upon a current connection strength to the another patient support apparatus. Stronger connection strengths are preferred over weaker connection strengths, although other factors may also influence the choice of the another patient support apparatus.

The first transceiver of the patient support apparatus may further be adapted to wirelessly receive data from a mattress positioned on the patient support apparatus.

According to another embodiment, a patient support apparatus is provided that includes a base, a frame, a patient support deck, an electronic memory, a control system, and a wireless transceiver. The frame is supported by the base, and the patient support deck is supported by the frame. The patient support deck is adapted to provide support for a patient. The control system controls a feature of the patient support apparatus and stores patient information in the electronic memory about a patient positioned on the patient support deck. The control system wirelessly transmits the patient information to another patient support apparatus via the wireless transceiver when the patient is transferred from the patient support apparatus to the another patient support apparatus.

According to other aspects, the control system may also receive patient information via the wireless transceiver when a patient is first transferred to the patient support apparatus. Such information is then be stored in the electronic memory. The received patient information may come from another patient support apparatus, or it may come from another source, such as, but not limited to, the healthcare computer network. If it comes from another source, a second wireless transceiver is included on the patient support apparatus for receiving the patient information.

A user control is included that controls when the control system wirelessly transmits the patient information to the another patient support apparatus. The patient information includes a patient identifier, and/or it includes information related to the patient's fall risk or susceptibility to bed sores. A display may be included on the patient support apparatus that displays an identifier of the another patient support apparatus to which the patient information is wirelessly transmitted. A scale system for weighing the patient that is built into the patient support apparatus may serve as a double checking mechanism such that the control system issues an alert if the patient information is transmitted to the another patient support apparatus without the scale system detecting an exit of the patient off of the patient support deck.

According to still another embodiment, a patient support apparatus is provided that includes a base, a frame, a patient support deck, a control system, and a wireless transceiver. The frame is supported on the base and the patient support deck is supported on the frame. The patient support deck provides support for a patient. The control system is adapted to control a feature of the patient support apparatus. The wireless transceiver wirelessly receives signals from another patient support apparatus and the signals include location information that indicates a location of that another patient support apparatus within a healthcare facility. The control system is adapted to use the location information, along with a measurement of a strength of the signals, to estimate a location of the patient support apparatus within the healthcare facility.

In other aspects, the wireless transceiver receives signals from a plurality of patient support apparatuses and use them, along with a measurement of their strength, to estimate a location of the patient support apparatus within the healthcare facility. The control system is able to transmit the estimate of the location of the patient support apparatus to a recipient using the wireless transceiver. Alternatively, the control system transmits the estimate of the location of the patient support apparatus to a healthcare network using a different wireless transceiver positioned on the patient support apparatus.

An electronic memory may be included that stores patient information about a patient positioned on the patient support deck, wherein the control system is further adapted to wirelessly transmit the patient information from the memory to a different patient support apparatus when the patient is transferred from the patient support apparatus to the different patient support apparatus. The patient support apparatus may further include a user control that enables a user to control when the wireless transceiver transmits the patient information, and a display that displays an identifier of the different patient support apparatus to which the patient information is transmitted. The patient information may include a patient identifier.

In still other aspects, the control system may wirelessly receive information via the transceiver from a different patient support apparatus about a feature of the different patient support apparatus, and the control system thereafter forwards the received information off of the patient support apparatus via the transceiver. The received and forwarded information includes any one or more of the following: a bed exit condition of the different patient support apparatus, a siderail condition of the different patient support apparatus, a height of the different patient support apparatus, a brake status of the different patient support apparatus, and an angular orientation of a component of the different patient support apparatus.

The transceiver may also receive medical device data from a medical device, and have the control system forward the medical device data off of the patient support apparatus via the transceiver. Alternatively, the control system is able to forward the medical device data off of the patient support apparatus via a different transceiver, wherein the control system chooses between the two transceivers for forwarding the information off of the patient support apparatus. The medical device may be any one of a ventilator, a vital signs monitor, a respirator, an infusion pump, an IV pump, a temperature sensor, and a blood oxygen saturation monitor.

A second wireless transceiver may be included on the patient support apparatus that is in communication with the control system, wherein the control system is able to forward the estimate of location of the patient support apparatus off of the patient support apparatus via the second wireless transceiver. The control system selects a recipient of the estimate of location based upon data received from a plurality of potential recipients wherein the data includes information about the communication capabilities of the potential recipients with a healthcare Ethernet.

According to still another embodiment, a system is provided for locating a plurality of patient support apparatuses within a healthcare facility. The system includes a plurality of stationary location devices, a plurality of patient support apparatuses in communication with at least one of the stationary location devices. The plurality of stationary location devices are positioned within a healthcare facility at known locations and the patient support apparatuses are adapted to determine information about their respective locations from communications with the stationary location devices. The system further includes at least one patient support apparatus that, when it is not in communication with any of the location devices, is able to determine its location relative to the plurality of patient support apparatuses by triangulating wireless signals received from the plurality of patient support apparatuses.

According to other aspects, the at least one patient support apparatus wirelessly transmits its determined location to a healthcare network. The stationary location devices communicate with the patient support apparatuses via infrared communications. Such communications may be physically limited to situations where the patient support apparatus is positioned within the same room as the stationary location device, and/or positioned within five to ten feet or less of a stationary location device.

In any of the embodiments, the patient support apparatus can be a bed, a stretcher, a recliner, a cot, or any other type of support structure used in a healthcare setting for providing support to a patient.

These and other features will be more fully understood and appreciated by reference to the detailed description of the embodiments below and the accompanying drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 8A is a plan view of a mesh network arrangement of a plurality of patient support apparatuses wherein a potential data path from a first patient support apparatus to an access point of a healthcare network is highlighted;

FIG. 8B is a plan view of the mesh network of FIG. 8A shown with one patient support apparatus removed and an alternative data path for transmitting data from the first patient support apparatus to the access point of the healthcare network;

DETAILED DESCRIPTION OF THE EMBODIMENTS

Figure 1:
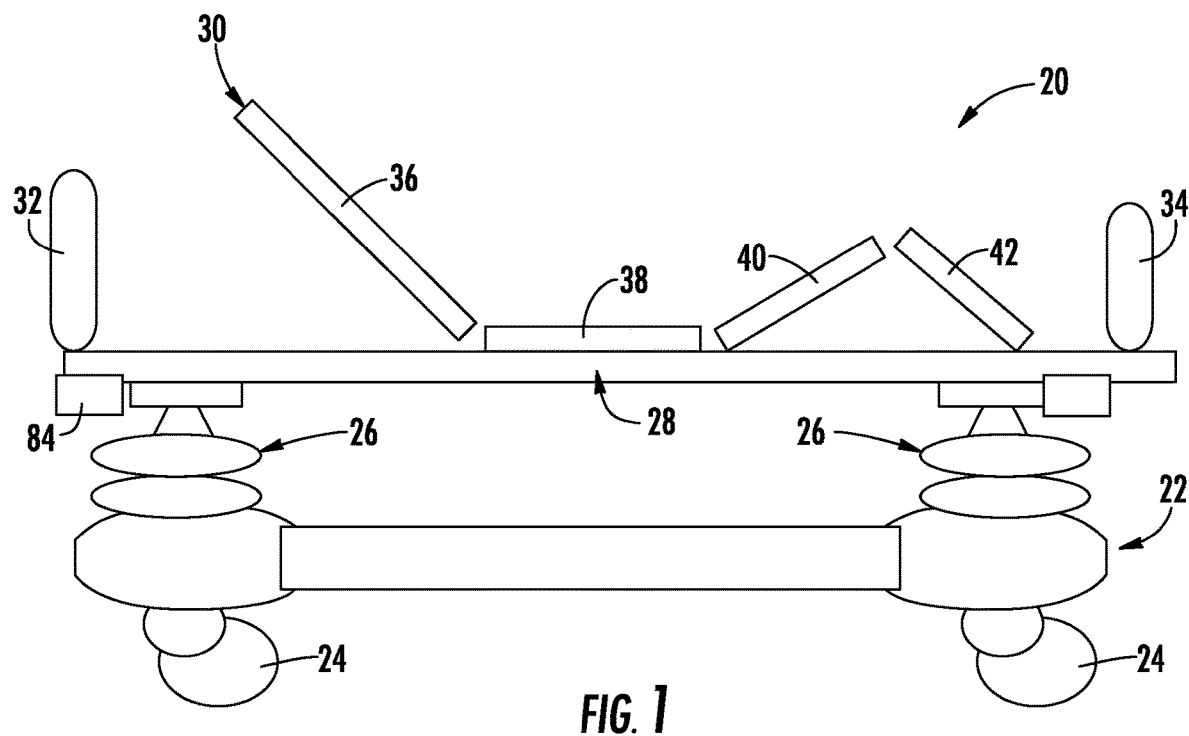
FIG. 1 is side elevational diagram of a patient support apparatus into which one or more of the features of the present invention may be incorporated.

A patient support apparatus 20 that may incorporate one or more of the aspects of the present invention is shown in FIG. 1. Patient support apparatus 20 may be a cot, a stretcher, a bed, a recliner, an operating table, or any other type of structure used to support a patient in a healthcare setting. In general, patient support apparatus 20 includes a base 22 having a plurality of wheels 24, a pair of elevation adjustment mechanisms 26 supported on said base, a frame 28 supported on said elevation adjustment mechanisms, and a patient support deck 30 supported on said frame. Patient support apparatus 20 further includes a headboard 32 and a footboard 34.

Base 22 includes a brake (not shown) that is adapted to selectively lock and unlock wheels 24 so that, when unlocked, patient support apparatus 20 may be wheeled to different locations. Elevation adjustment mechanisms 26 are adapted to raise and lower frame 28 with respect to base 22. Elevation adjustment mechanisms 26 may be hydraulic actuators, electric actuators, or any other suitable device for raising and lowering frame 28 with respect to base 22. In some embodiments, elevation adjustment mechanisms 26 are operable independently so that the orientation of frame 28 with respect to base 22 can also be adjusted.

Frame 28 provides a structure for supporting patient support deck 30, headboard 32, and footboard 34. Patient support deck 30 provides a surface on which a mattress (not shown), or other soft cushion is positionable so that a patient may lie and/or sit thereon. Patient support deck 30 is made of a plurality of sections, some of which are pivotable about generally horizontal pivot axes. In the embodiment shown in FIG. 1, patient support deck 30 includes a head section 36, a seat section 38, a thigh section 40, and a foot section 42. Head section 36, which is also sometimes referred to as a Fowler section, is pivotable between a generally horizontal orientation (not shown in FIG. 1) and a plurality of raised positions (one of which is shown in FIG. 1). Thigh section 40 and foot section 42 may also be pivotable, such as is shown in FIG. 1.

Although not illustrated in the patient support apparatus 20 depicted in FIG. 1, patient support apparatus 20 will sometimes include a plurality of siderails (not shown) coupled to frame 28. If patient support apparatus 20 is a bed, there are typically four such siderails, one positioned at a left head end of frame 28, a second positioned at a left foot end of frame 28, a third positioned at a right head end of frame 28, and a fourth positioned at a right foot end of frame 28. If patient support apparatus 20 is a stretcher or a cot, there are typically fewer siderails. In other embodiments, there are no siderails on patient support apparatus 20. Regardless of the number of siderails, such siderails are movable between a raised position in which they block ingress and egress into and out of patient support apparatus 20, and a lowered position in which they are not an obstacle to such ingress and egress.

The construction of any of base 22, elevation adjustment mechanisms 26, frame 28, patient support deck 30, headboard 32, footboard 34, and/or the siderails may be the same as disclosed in commonly assigned, U.S. Pat. No. 7,690,059 issued to Lemire et al., and entitled HOSPITAL BED, or as disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION; or as disclosed in the Stryker Maintenance Manual for the Model 3002 S3 MedSurg Bed, available from Stryker Corporation of Kalamazoo, Mich., the disclosures of all three of these which are incorporated herein by reference. The construction of any of base 22, elevation adjustment mechanisms 26, frame 28, patient support deck 30, headboard 32, footboard 34 and/or the siderails may also take on forms different from what is disclosed in the aforementioned documents.

Patient support apparatus 20 of FIG. 1 further includes a mesh network node 84 that allows apparatus 20 to form an ad hoc electrical communications network with one or more other patient support apparatuses 20 and/or one or more medical devices. Each of the other patient support apparatuses 20 and/or medical devices includes similar electronics that form a mesh network node that is able to communicate with node 84, as well as any other nodes 84 on other apparatuses 20 or medical devices that are within communication range. Each node 84—whether positioned on a patient support apparatus 20, a medical device, or something else—is therefore able to not only disseminate data that originates from the structure to which it is coupled, but also to serve as a relay for forwarding information it receives from other nodes onto to still other nodes, or onto a healthcare network 70 (FIG. 10), as will be described in greater detail below. Further, because the positions of patient support apparatus 20, as well as medical devices and other structures, are likely to change over time, the mesh network formed by the nodes 84 is dynamic such that the data paths change with changing locations and/or other conditions.

Figure 2:
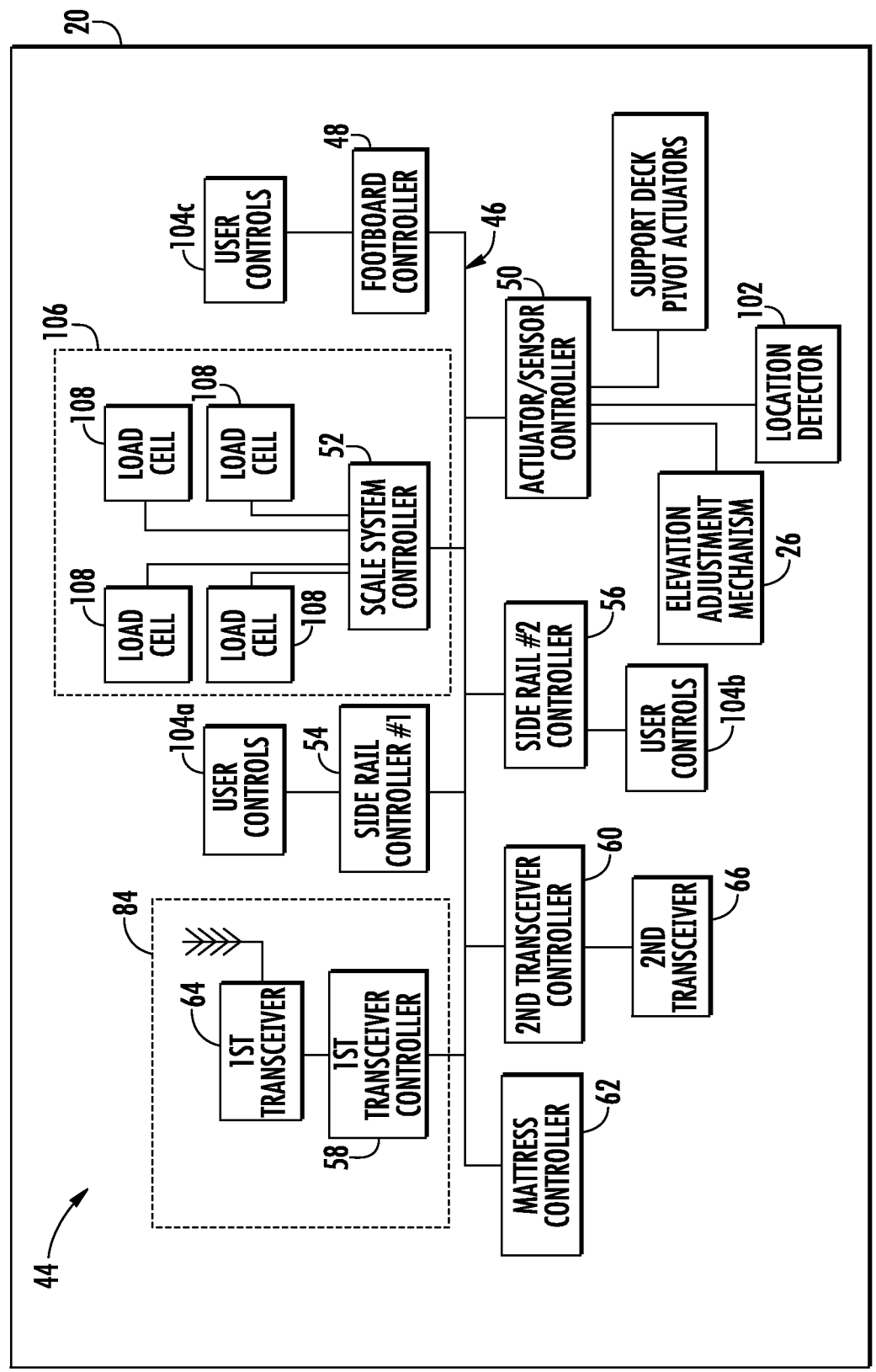
FIG. 2 is a diagram of one embodiment of an electrical control system that may be used with the patient support apparatus of FIG. 1, or with any of the other patient support embodiments described herein.

FIG. 2 illustrates one embodiment of an electrical control system 44 that is incorporated into patient support apparatus 20. Electrical control system 44 includes, in the illustrated embodiment, an internal communications network 46. Internal communications network 46 is a Controller Area Network, although it will be understood by those skilled in the art that it could be another type of network, such as, but not limited to, a CANOpen network, DeviceNet network, other networks having a CAN physical and data link layer), a LONWorks network, a Local Interconnect Network (LIN), a FireWire network, or any other known network for communicating messages between electronic structures on patient support apparatus. Internal communications network 46 includes a number of controllers or internal nodes that are in communication with each other over the internal network 46. These include a footboard controller 48, an actuator/ sensor controller 50, a scale system controller 52, a first side rail controller 54, a second side rail controller 56, a first transceiver controller 58, a second transceiver controller 60, and a mattress controller 62. Before describing in further detail the structure and functions of these controllers, it should be pointed out that patient support apparatus 20 could alternatively be designed without any internal communications network, but instead have various controllers communicate with each other in a non-networked manner, or by combining the functions of these various controllers into one controller that handles all of these tasks, or in still other manners that do not utilize any sort of communications network on the patient support apparatus 20.

Each controller that communicates over internal communications network 46 includes one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art.

In the embodiment of FIG. 2, the electrical control system 44 of patient support apparatus 20 includes a first transceiver 64 that is electrically and communicatively coupled to a first transceiver controller 58, as well as a second transceiver 66 that is electrically and communicatively coupled to second transceiver controller 60. It will be understood by those skilled in the art that the use of the terms "first transceiver" and "second transceiver" herein has been done for communicative convenience, and that in no way do the "first" and "second" labels connote any significance to, or ranking of, the respective transceivers, nor are they intended to suggest a limit to the number of transceivers that may be present on a given patient support apparatus 20.

First transceiver controller 58 is adapted to process messages that are communicated on electrical communications network 46 that are intended for first transceiver controller 58. Such messages will typically, although not exclusively, include messages containing data that is meant to be transmitted off of patient support apparatus 20 via first transceiver 64. Similarly, second transceiver controller 60 is adapted to process messages that are communicated on electrical communications network 46 that are intended for second transceiver controller 60. Such messages will typically, although not exclusively, include messages containing data that is meant to be transmitted off of patient support apparatus 20 via second transceiver 66. First and second transceiver controllers 58 and 60 are further adapted to process messages received by first and second transceivers 64 and 66, respectively, and, where applicable, forward the content of those messages onto internal communications network 46 for sharing with one or more of the various controllers on network 46.

Together, first transceiver 64 and first transceiver controller 58 form mesh network node 84. Transceiver 64 therefore receives messages and/or signals from other transceivers that are meant to be forwarded off of patient support apparatus 20, rather than consumed by patient support apparatus 20. Controller 58 processes the received messages sufficiently to determine whether the messages are for internal consumption or whether they are to be relayed onto another recipient. Messages that are to be relayed are temporarily stored in memory that is accessible to controller 58 until such messages have been successfully forwarded onto another recipient. Messages that are to be consumed by patient support apparatus 20 are processed by controller 58 and directly delivered to the appropriate device on patient support apparatus 20 by hardwire or other direct connection, or their content is distributed via internal communications network 46 for use by one or more of the controllers on network 46.

In one embodiment of patient support apparatus 20, first and second transceivers 64 and 66 are different types of transceivers. That is, each transceiver is adapted to transmit and receive electrical signals using two different communication protocols. For example, in one embodiment, first transceiver 64 is adapted to transmit and receive wireless electrical signals using the Zigbee protocol, or the IEEE 802.15.4 protocol, while the second transceiver 66 is adapted to transmit and receive wireless electrical signals using the Wi-Fi protocol, or the IEEE 802.11 protocol. In other embodiments, first transceiver 64 uses the Zigbee or IEEE 802.15.4 protocol while second transceiver 66 is adapted to transmit and receive electrical signals over a wire or cable connected to patient support apparatus 20. Such a wire or cable may constitute a universal serial bus (USB) connection, or it may include an RS-232 or RS-485 connection, or it may include a wired Ethernet cable. In still other embodiments, still other communication protocols are used instead of those listed herein, whether wired or wireless, including, but not limited to, infrared communication, Bluetooth communication, and other types of communication.

Regardless of the specific communications format used, first transceiver 64 is designed to communicate with one or more nearby structures, such as, but not limited to, medical devices, sensing systems, and/or with other patient support apparatuses. First transceiver 64 therefore sends messages to and receives messages from medical devices equipped with transceivers that are compatible with first transceiver 64, and/or it sends messages to and receives messages from sensing systems equipped with compatible transceivers, and/or it sends messages to and receives messages from other first transceivers positioned on one or more other patient support apparatuses.

If communicating with another patient support apparatus, the other patient support apparatus need not be identical to patient support apparatus 20, but instead merely has to be able to have the ability to send and receive messages using the same protocol used by first transceiver 64. Thus, in some situations, if patient support apparatus 20 is a bed, it is able to communicate via first transceiver 64 with a stretcher, or with a cot, or a recliner, or some other type of patient support apparatus that is of a different physical type than a bed. Further, even if the other patient support apparatus is a bed, it need not be constructed in the same manner as patient support apparatus 20. It may be a different model of bed in some cases, or it may be made by a different manufacturer in some cases, or it may be of the exact same type of bed as patient support apparatus 20. The same is true if patient support apparatus 20 is a cot, a stretcher, a recliner, or something else—the other patient support apparatuses to which it communicates via first transceiver 64 may be the same or a different type of patient support apparatus.

Figure 7:
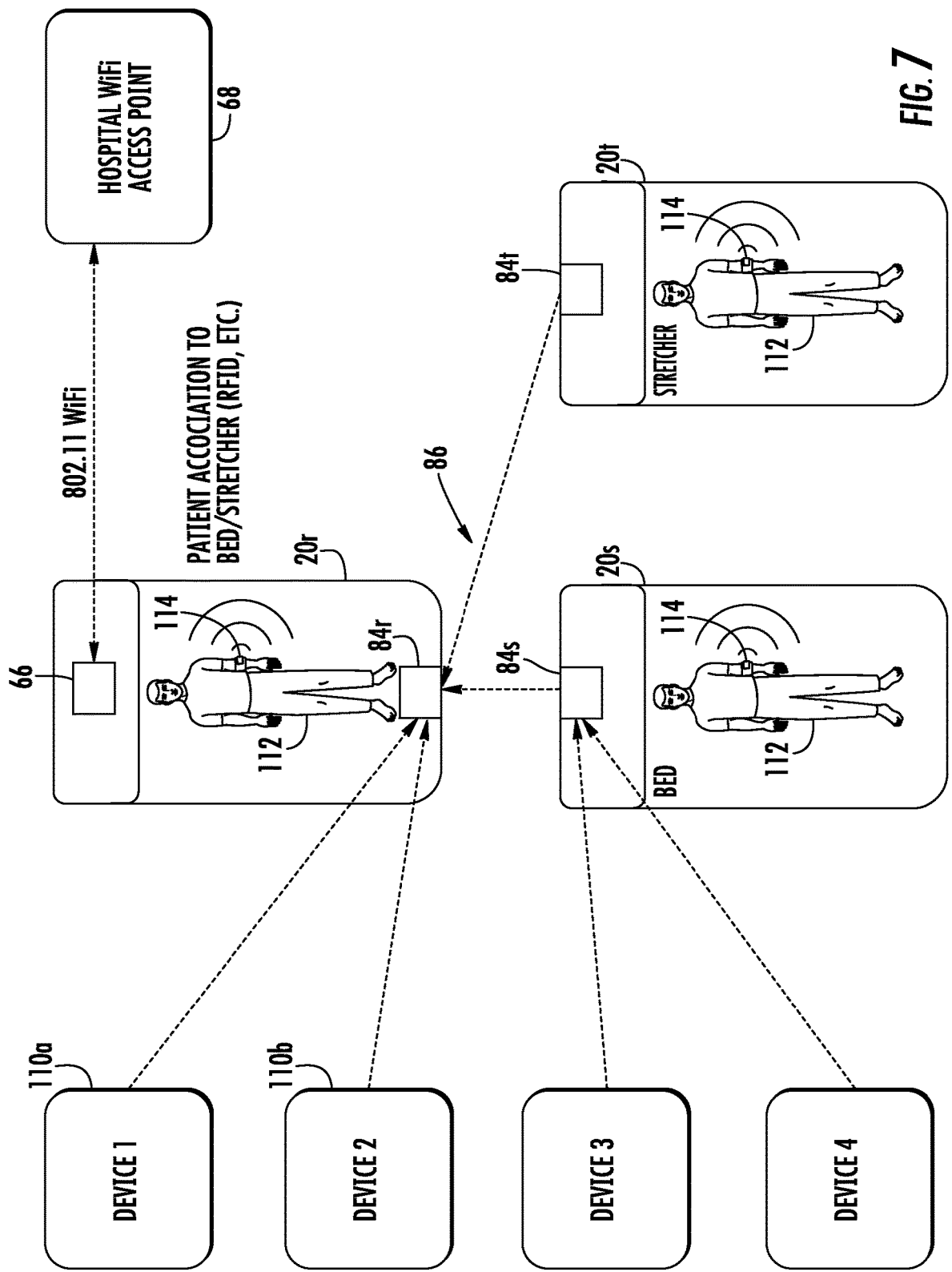
FIG. 7 is a plan view of a plurality of patient support apparatuses that are configured to receive data from one or more medical devices positioned within the vicinity of the patient support apparatuses, and to forward the data to a healthcare network access point.
Figure 10:
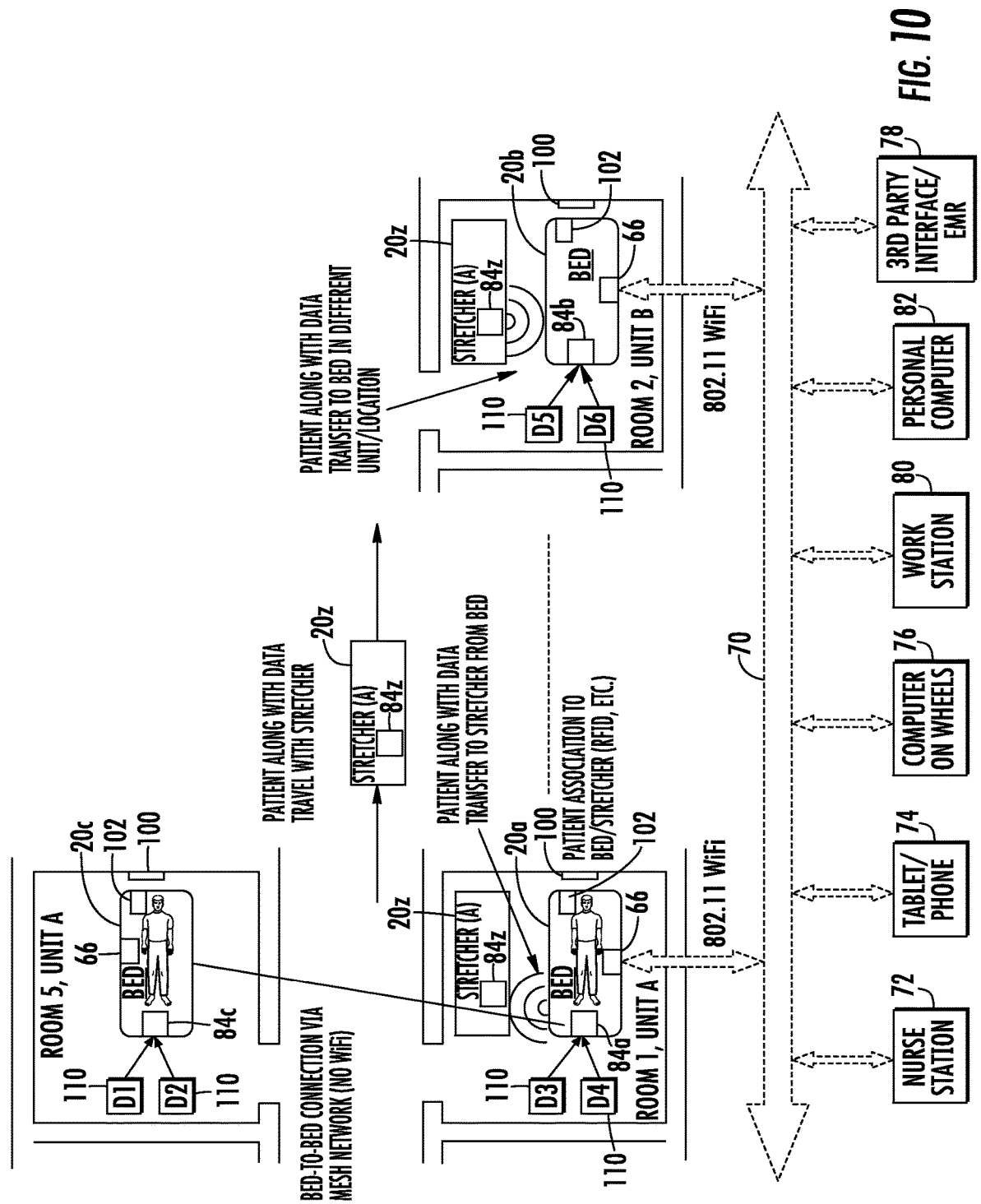
FIG. 10 is a plan view diagram of an arbitrary portion of a floor plan of a healthcare facility showing patient support apparatuses that are configured to wirelessly receive and transmit medical data, patient data, and other signals from other patient support apparatuses.

As noted, in some embodiments, first transceiver 64 is also configured to communicate with one or more medical devices 110 (see, e.g. FIG. 7 or 10). Such medical devices include any medical devices that are usable in a healthcare setting in a patient's room, or otherwise within a nearby vicinity of a patient positioned on a patient support apparatus 20. A non-exhaustive list of such potential medical devices includes ventilators, vital signs monitors, respirators, infusion pumps, IV pumps, temperature sensors, and/or blood oxygen saturation monitors. When communicating with these medical devices, first transceiver 64 and its associated controller 58—which together form one mesh network node 84—become part of a mesh network that includes other nodes 84. In such cases, node 84 of support apparatus 20 is able to relay information received from the medical devices 110 onto a healthcare communication network 70. This relay is able to take place via different routes. First, the relay of information may take place via a direct connection between the support apparatus 20 and network 70, or this relay of information may be routed through one or more other support apparatuses 20 before it is delivered to network 70. These alternative routes are selected by the nodes 84 and intelligence shared between them regarding signal strength, traffic, and/or other factors, as will be discussed more below.

In still other embodiments, first transceiver 64 of patient support apparatus 20 is configured to communicate with sensing systems that are used to sense one or more characteristics, features, conditions, and/or states of the caregiver, the patient, or other personnel. For example, in one embodiment, such a sensing system includes an interface pressure sensing sheet position on top of a mattress on the patient support apparatus 20, such as disclosed in commonly assigned U.S. patent application serial number PCT/US12/27402 filed Mar. 2, 2012 by applicants Balakrishnan et al., and entitled SENSING SYSTEM FOR PATIENT SUPPORTS, the complete disclosure of which is incorporated herein by reference. In such an embodiment, first transceiver 64 is configured to communicate with any one or more of the sensor array 22, the controller 24, the user interface 26, the sensor controller 28, and/or the tablet 44 disclosed in the PCT/US12/27402 patent application. The data from the interface pressure sensing system is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the interface pressure sensing system is partially or wholly consumed by patient support apparatus 20, or a device positioned on patient support apparatus 20.

In another embodiment, first transceiver 64 is configured to communicate with a video monitoring system, such as that disclosed in commonly assigned U.S. patent application Ser. No. 13/242,022 filed Sep. 23, 2011 by applicants Derenne et al. and entitled VIDEO MONITORING SYSTEM, the complete disclosure of which is hereby incorporated herein by reference. In such an embodiment, first transceiver 64 is configured to communicate with any one or more of the cameras 22, computer devices 24, and/or image projectors 30 disclosed in the Ser. No. 13/242,022 patent application. The data from the video system and/or cameras is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the video monitoring system is partially or wholly consumed by patient support apparatus 20, or a device positioned on patient support apparatus 20.

In still another embodiment, first transceiver 64 is configured to communicate with hand washing stations, or other devices, such as disclosed in commonly assigned U.S. patent application Ser. No. 13/570,934, filed Aug. 9, 2012, by applicants Hayes et al., and entitled PATIENT SUPPORT APPARATUS WITH IN-ROOM DEVICE COMMUNICATION, the complete disclosure of which is hereby incorporated herein by reference. In such an embodiment, first transceiver 64 is configured to communicate with any of the electronic tags 24 (e.g. mobile tags 24a, stationary tags 24b, and patient tags 24c) and/or the transceiver 52 disclosed in the Ser. No. 13/570,934 application. The data from the hand washing station, or other device, is forwarded via mesh network node 84 of patient support apparatus 20 onto healthcare network 70, either directly from support apparatus 20, or via one or more additional support apparatuses 20 or other types of intermediate mesh network nodes 84. Still further, in some embodiments, the data from the hand washing station is partially or wholly consumed by patient support apparatus 20, or a device positioned on patient support apparatus 20. In yet other embodiments, the patient hand washing station is configured to be, or include, a mesh network node itself, in which case the hand washing station may be the recipient of data relayed off of patient support apparatus 20 that is destined for communication to healthcare network 70.

In still other embodiments, first transceiver 64 is configured to communicate with any combination of the devices disclosed herein, including, but not limited to, any of those disclosed in the patent references incorporated herein by reference. Still further, patient support apparatus 20 may be modified to include a third or fourth transceiver that, instead of, or in addition to, first transceiver 64, communicates with any of the devices disclosed herein, including, but not limited to, any of those disclosed in the patent references incorporated herein by reference.

Second transceiver 66, as noted earlier, is configured to communicate with one or more wireless access points 68 of a healthcare communications network 70. An example of one such communications network 70 is shown in FIG. 10. Such a network is often an Ethernet network, although it may use other networking communication protocols. The devices, applications, and/or servers that are coupled to the network 70 will vary from facility to facility because they will be dependent upon a particular healthcare institution's choice of what third-party software and/or systems they have installed on their network. In the illustrative embodiment shown in FIG. 10, network 70 includes a plurality of nurses stations 72, tablet and/or phones 74, computers on wheels (COW) 76, work stations 80, and one or more personal computers 82. An electronic medical records (EMR) server 78 may also be included. As noted, network 70 may further include one or more additional devices, applications, and/or servers, or it may include one or fewer devices, applications, and/or servers, depending upon the particular configuration that has been implemented at a particular healthcare facility. Such additional devices, applications, and/or servers may include an Admission, Discharge, and Transfer (ADT) system that manages the admission, discharge, and transfer of patients in the healthcare facility; a workflow server that manages the work assignments of caregivers in the healthcare facility; and/or wireless alerting system that automatically forwards alarms and alerts to appropriate healthcare personnel via wireless communication technology. Such wireless communication technology may include the forwarding of alerts via cell phones, WIFI devices, pagers, personal digital assistants (PDAs), or by other means. Any information that is transmitted to network 70 via one or more of the mesh network nodes 84 may therefore cause an alert to be forwarded to the appropriate caregiver(s), depending upon the contents of such information. The nurses station 72, tablets 74, computers on wheels 76, work stations 80, personal computers 82, electronic medical record systems 78, ADT systems, work flow systems, and wireless alerting systems may all be conventional products that are commercially available from one or more different suppliers, as would be known to one of ordinary skill in the art.

Figure 3:
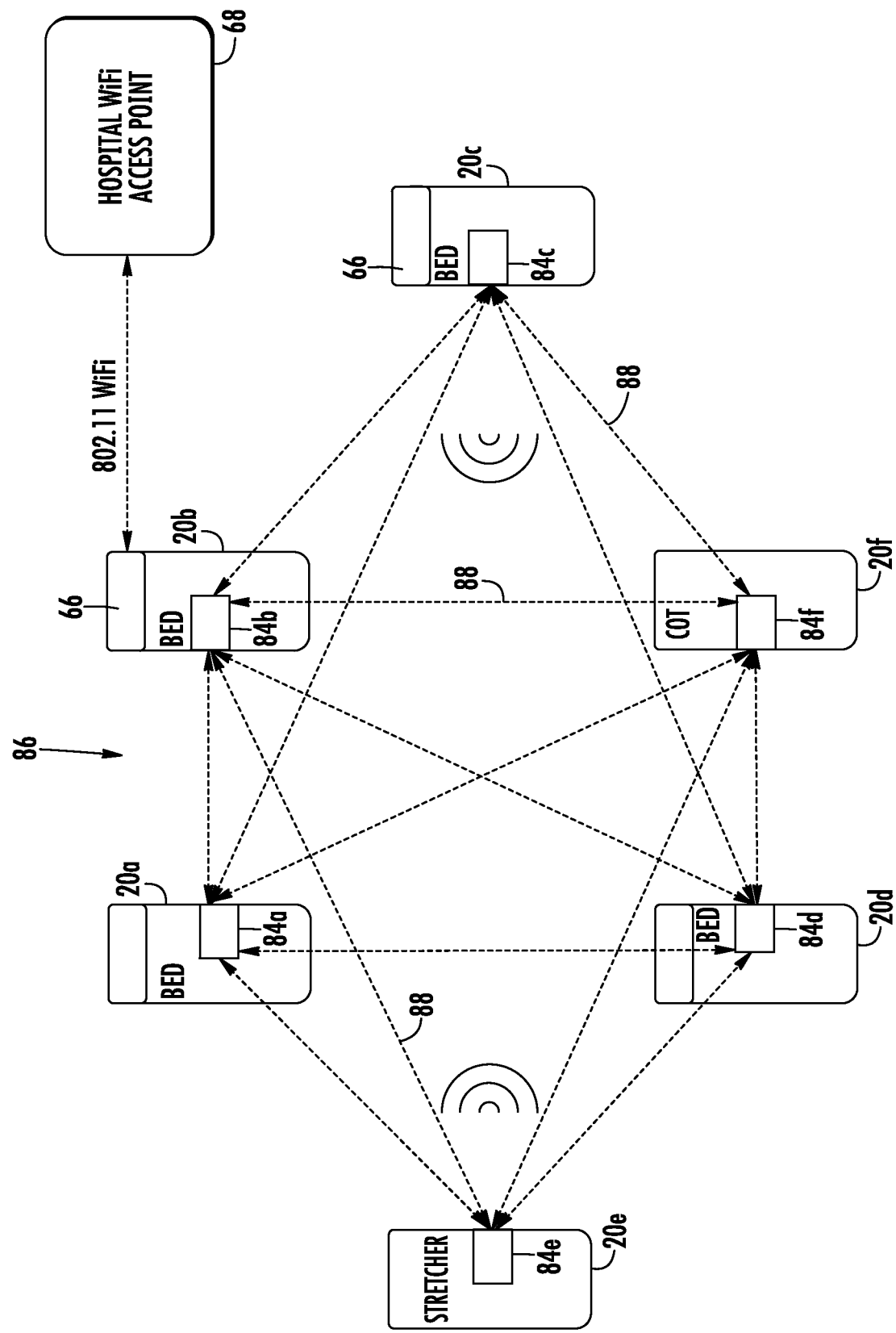
FIG. 3 is a plan view diagram of a plurality of patient support apparatuses according to one embodiment showing a mesh network that enables the patient support apparatuses to communicate with each other and/or an access point of a healthcare network.

FIG. 3 illustrates an arbitrary example of a mesh network 86 that created by a plurality of patient support apparatuses and their respective mesh network nodes 84. In the example shown, the mesh network 86 includes four patient support apparatuses 20 that are beds (20*a*, 20*b*, 20*c*, and 20*d*), one patient support apparatus 20 that is a stretcher (20*e*), and one patient support apparatus 20 that is a cot (20*f*). Each patient support apparatus 20 includes a mesh network node 84 that comprises first transceiver 64 and first transceiver controller 58. Each node 84 broadcasts signals that are responded to by all of the other nodes that are sufficiently close to receive the broadcasted signals. This broadcasting and responding enables each patient support apparatus 20 to determine what other patient support apparatuses 20 are within communication distance. When responding to such broadcasts, a node 84 also responds with information identifying what nodes 84 it itself is in communication distance with. For example, if stretcher 20*e* sends out an initial broadcast, beds 20*a*, 20*b*, and 20*d*, along with cot 20*f*, will respond because they are all sufficiently close to be within communication range of stretcher 20*e* (for purposes of discussion, it will be assumed that bed 20*c* is out of direct communication range with stretcher 20*e*). The response from beds 20*a*, 20*b*, and 20*d* and cot 20*f* includes information indicating the nodes that each of these apparatuses 20 are in communication with. Thus, for example, bed 20*a* might respond to stretcher 20*e* by indicating that it is able to communicate with bed 20*b*, bed 20*c*, cot 20*f*, and bed 20*d*. Similarly, bed 20*d* might respond to stretcher 20*e* by indicating that it is able to communicate with beds 20*a*, 20*b*, and 20*c*, as well as cot 20*f*. Still further, in addition to forwarding information about what nodes a particular node is currently able to communicate with, information identifying the relative signal strengths of each of the currently available nodes is also included. In this manner, routing of the information can be accomplished by selecting routes having relatively higher signal strengths, or at least signal strengths above a predetermined threshold, thereby ensuring that more bandwidth is available for transmitting information.

In some embodiments, the response back to stretcher 20*e* also includes information indicating whether any of the nodes 84 are able to communicate with a wireless access point 68 of healthcare network 70. Thus, for example, bed 20*a* might respond to stretcher 20*e* by indicating that not only is it able to communicate with beds 20*b*, 20*c*, and 20*d*, and cot 20*f* (and also their signal strengths), but also that bed 20*b* is able to communicate directly with a wireless access point 68, which, in the example of FIG. 3, is a WiFi access point, although it will be understood by those skilled in the art that other types of access points could be used. Because beds 20*c* and 20*d*, as well as cot 20*f*, are all in communication with bed 20*b*, they too might all respond to stretcher 20*e* with information indicating that bed 20*b* is in direction communication with access point 68. Each apparatus 20 is therefore able to include in its response to stretcher 20*e* an indication that it is or that it is not is direct communication with a wireless access point, as well as a similar indication for all of the apparatuses it is in communication with. Depending upon the size of the mesh network 86, additional levels of communication abilities may be provided for nodes 84 that are even further downstream from stretcher 20*e*.

In addition to responding to stretcher 20*e*'s initial broadcast, each apparatus 20 that is within communication distance may also respond with additional information that may be useful for stretcher 20*e*. As was noted, such additional information may include information about the signal strength of each of the communication channels between apparatuses 20, and/or the signal strength between an apparatus 20 and an access point 68. Such additional information alternatively, or additionally, includes information indicating a current level of communication traffic and/or information backlog and/or available bandwidth and/or the congestion that a node is experiencing. Still further, such information includes information that uniquely identifies each node, and/or information that uniquely identifies each patient support apparatus 20.

All of the information that stretcher 20*e* receives in response to its initial broadcast message is stored in a memory accessible to first transceiver controller 58. This information enables controller 58 to determine which route, or portion of a route, is the best route for transmitting data to access point 68. That is, stretcher 20*e* uses the information it receives from the other nodes (e.g. 84*a*, 84*b*, 84*d*, and 84*f*) to select an initial recipient of any data that it needs to forward to network 70 (which would be via access point 68 in FIG. 3, although there may be multiple access points in other examples). Once this initial recipient is chosen, node 84*e* of stretcher 20*e* transmits the desired information to that recipient, which then forwards the information onto access point 68, either directly or by some other route, depending upon circumstances. In some embodiments, the original source of the transmitted information (in this example, stretcher 20*e*) includes information indicating its preferred complete routing path to access point 68, while in other embodiments, the original source of the transmitted information only chooses the initial recipient of the transmitted data and leave subsequent routing decisions to the discretion of the recipient node and any other downstream nodes that relay the information to access point 68.

As was noted, the choice of the initial recipient of the information is made based upon any one or more of the items of information received from the other nodes. The choice of the initial recipient may also be combined with predefined data or programming instructions. Such predefined data or programming instructions may, for example, dictate that, absent extenuating circumstances, an apparatus 20 will try to communicate information to access point 68 in the most direct route (i.e. the route involving the fewest number of communications hops between the source of the data and network 70). Thus, as an example, stretcher 20*e* may be programmed to initially select by default bed 20*b* as the initial recipient of its transmitted data because bed 20*b* is in direct communication with access point 68. However, such programming could also take into account the signal strength of the communication path 88 between stretcher 20*e* and bed 20*b* and, if it is below a desired threshold level, cause node 84*e* to seek an alternate initial recipient with which it has a communication path 88 having a stronger signal. Stretcher 20*e* may therefore, as an example, determine that path 88 between stretcher 20*e* and bed 20*b* is too weak, and therefore choose to initially send its data to bed 20*a*. This choice of bed 20*a* as an alternative to the default initial recipient may be based upon any of the information stretcher 20*e* has received from the other nodes 84. Thus, the choice of bed 20*a* as the alternative initial recipient of the data from stretcher 20*e* may be made, for example, because the communication path 88 between stretcher 20*e* and bed 20*a* is stronger than any of the other communication paths stretcher 20*e* has with the other patient support apparatuses 20*c*, 20*d*, and 20*f*.

The data that is able to be transmitted from a patient support apparatus 20 includes a variety of different types of data, some of which will be discussed in greater detail below. In some embodiments, data about one or more sensors and/or systems on the patient support apparatus 20 is communicated. Such data includes information indicating whether the side rails of a patient support apparatus are up or down; whether the brake is locked or unlocked; the height of the frame 28 or patient support deck 30 above the base 22 (in those apparatuses where this height can be changed by a user); the angle of one or more sections of deck support 30 (such as head section 36—which may be useful to know for helping to prevent ventilator associated pneumonia and/or for other purposes); the output from a bed exit system that is incorporated into patient support apparatus 20 (such as, but not limited to, the bed exit system disclosed in commonly-assigned U.S. Pat. No. 5,276,432 issued to Travis and entitled PATIENT EXIT DETECTION MECHANISM FOR HOSPITAL BED, the complete disclosure of which is hereby incorporated herein by reference); information indicating whether a bed exit system is armed or disarmed; the output from a patient movement detection system that is incorporated into patient support apparatus 20 (such as, but not limited to, the patient movement detection system disclosed in commonly-assigned U.S. Pat. No. 6,822,571 issued to Conway and entitled PATIENT MOVEMENT DETECTION SYSTEM FOR A BED INCLUDING A LOAD CELL MOUNTING ASSEMBLY, the complete disclosure of which is also incorporated herein by reference); the output from a patent interface pressure detection system (such as, but not limited to, that disclosed in the PCT/US12/27402 application filed Mar. 2, 2012, discussed above); data from one or more medical devices that are either supported on apparatus 20, or in communication with apparatus 20 (such as via first transceiver 64); information from a video monitoring system (such as that disclosed in the Ser. No. 13/242,022 patent application mentioned above); and information from other devices or structures in the room that have wireless communication abilities (such as, but not limited to, the devices disclosed in the Ser. No. 13/570,934 application discussed above.

Any of the data that is transmitted from a patient support apparatus 20 is data that originates from that particular patient support apparatus, or it is data that is received from another patient support apparatus 20 that is to be relayed onto another node 84 or an access point 68. Regardless of whether the data that is to be transmitted originates from the support apparatus 20, or was received from another support apparatus 20, the algorithms used for determining the next recipient of the data are the same. Thus, for example, in the arbitrary example discussed above with respect to FIG. 3 wherein stretcher 20e is transmitting data that is to be forwarded to access point 68, the logic used by stretcher 20e to determine the initial recipient of its data is the same, regardless of whether the transmitted data originated from stretcher 20e, or it was received by stretcher 20e from another support apparatus (such as, for example, bed 20d). Similarly, once stretcher 20e transmits the data to an initial recipient (e.g. bed 20a), that recipient utilizes the same logic and/or algorithms that stretcher 20e used in deciding what node to forward the data to.

By forwarding information through mesh network 86 to access point 68, the information is able to avoid bottlenecks, route around weak communication channels, and in some cases (such as discussed below with respect to FIG. 4) avoid areas where communication with access point 68 is not possible. The routing algorithms used therefore ensure that data is efficiently, yet effectively, transferred to the healthcare network 68 so that the appropriate servers and/or applications on the network 68 can used the transmitted data in the desired manner.

Figure 4:
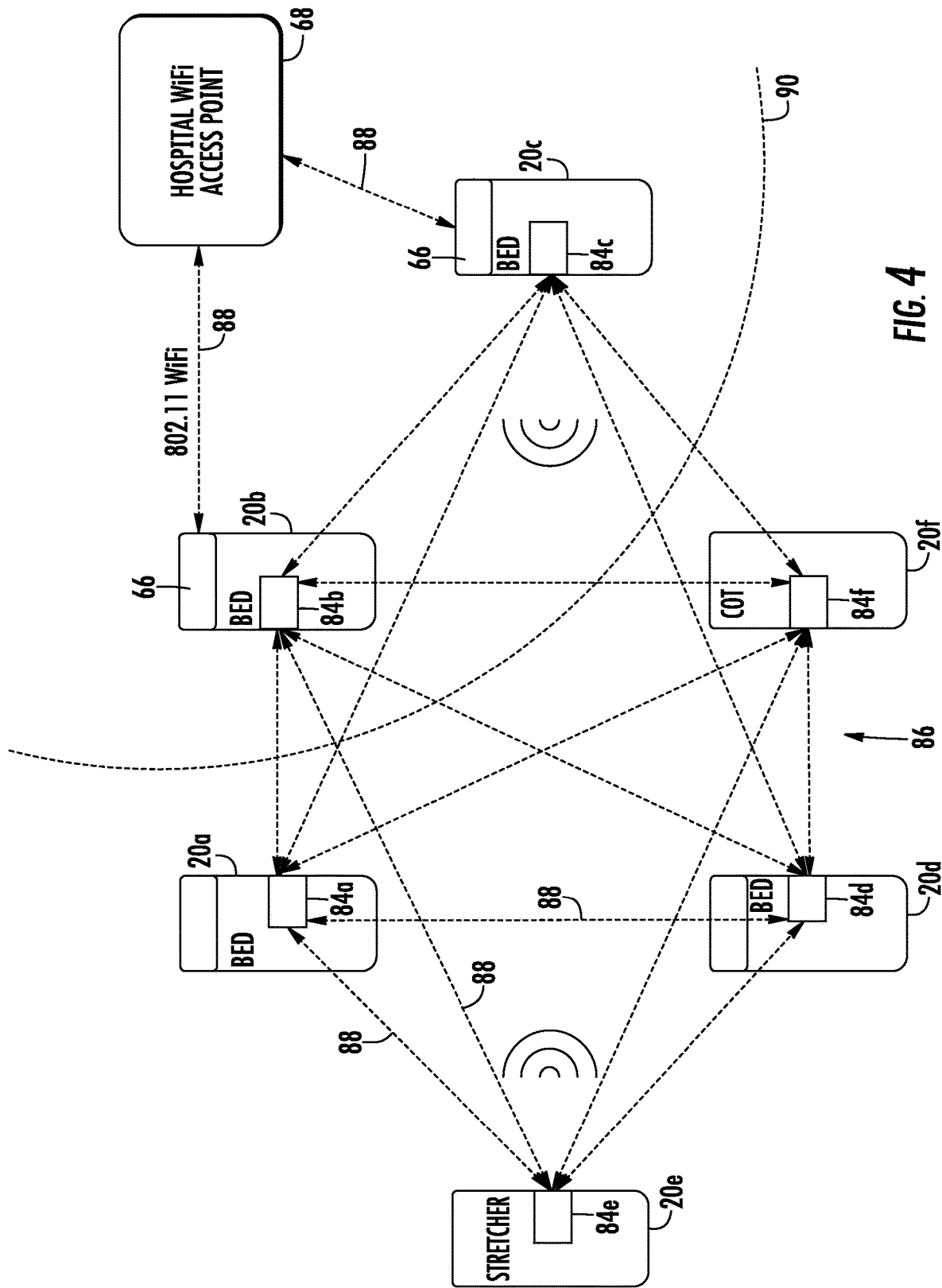
FIG. 4 is an plan view diagram similar to FIG. 3 showing how the mesh network may be used to forward information from patient support apparatuses outside a range of the access point to one or more other patient support apparatuses that are within range of the access point.

FIG. 4 illustrates another arbitrary example wherein some of the patient support apparatuses 20 and associated nodes 84 are completely outside the communication range of access point 68. In the example of FIG. 4, a boundary line 90 indicates the furthest extent of the communication range of access point 68. Thus, only beds 20b and 20c are within communication range of access point 68. Any information to be transmitted from beds 20a and 20d, or cot 20f and stretcher 20e to network 70 must therefore pass (in this example) through either bed 20b or bed 20c. By enabling patient support apparatuses 20 to communicate over, and form, a mesh network 86, the communication range of access point 68 is effectively extended. That is, because those apparatuses 20 within range of access point 68 (e.g. beds 20b and 20c) can talk to apparatuses outside of range 90 and relay information from these apparatuses 20 to access point 68, the effective communication range of access point 68 is enlarged. This allows healthcare facilities to avoid the expensive extra infrastructure that might otherwise be necessary to provide sufficient communication abilities throughout a facility (i.e. it may not be necessary to install as many wireless access points 68 in a given facility when the facility uses the mesh-network equipped patient support apparatuses 20 disclosed herein).

When a patient support apparatus 20 is forwarding data to network 70 via mesh network 86 and there are multiple patient support apparatuses 20 in direct communication with one or more access points 68 (such as, for example, the situation illustrated in FIG. 4), the choice of which apparatus 20 to forward data to may be made in the same manner as discussed above. That is, in the example of FIG. 4, the choice between routing data through bed 20b or 20c is based upon one or more of the following: a default preferred path, relative signal strengths, available bandwidth, traffic congestion, communication backlogs, and/or other factors. If such factors present an equal case for routing through beds 20b and 20c, then the ultimate choice may be based on a random selection, or some other factor.

In the examples of FIGS. 3 and 4, the data transmitted from a support apparatus 20 to access point 68 has been ultimately transmitted to access point 68 via a second transceiver 66 on one of patient support apparatuses 20. If that data has been received from another patient support apparatus 20 (and is thus being relayed to access point 68), the receipt of data is via first transceiver 64. Thus, mesh network communications is accomplished via first transceivers 64, while communications with one or more access points 68 is via second transceivers 66.

It will be understood by those skilled in the art that all of the first transceivers 64 do not have to be identical to each other. Similarly, it will be understood by those skilled in the art that all of the second transceivers 66 do not have to be identical to each other. If disparate types of first and/or second transceivers 64 and/or 66 are incorporated into the support apparatuses 20 of a given mesh network 86, then the communication abilities of the transceivers may also be relayed to each of the nodes and used in the algorithms for determining routing. For example, in some embodiments, some patient support apparatuses have a second transceiver 66 that is able to communicate in accordance with IEEE 802.11b standards, while other patient support apparatuses 20 are able to communicate in accordance with IEEE 802.11g or 802.11n standards, both of which are faster than 802.11b standards. This information is factored into the algorithms for choosing the most efficient routing of data to network 70.

Mesh network 86 is also useful for disseminating data from one or more sources on healthcare network 70. When disseminating such data, the same or similar algorithms can used for routing the data through mesh network 86 to the appropriate destination. Such disseminated data includes, but is not limited to, patient information (such as, but not limited to, information that identifies a particular patient who is occupying a particular patient support apparatus), caregiver information (such as, but not limited to, information identifying the what caregiver(s) have been assigned to a particular patient, room, or support apparatus 20), medical information (such as, but not limited to, information about the fall risk or a patient, information about the susceptibility of a patient to bed sores—such as a Braden scale rating, information and/or any other relevant medical information about a particular patient), commands (such as, but not limited to, commands to change the status of a system or component on patient support apparatus 20), requests for data, acknowledgements, and/or any other type of data that is desirably communicated to one or more patient support apparatuses 20, or to any of the devices or other structures that a patient support apparatus 20 is in communication with via one or more of its transceivers.

Each node 84 of mesh network 86 is configured to dynamically and regularly update its communication abilities and/or status so that the routing of data through mesh network 86 is dynamically adapted to changing conditions. Such changing conditions can include, for example, the movement of one or more patient support apparatuses 20 to different locations, traffic congestion, the addition or deletion of one or more data sources or destinations (e.g. one or more medical devices or support apparatuses 20), and/or any other conditions that might usefully influence the efficient routing of data through mesh network 86.

FIGS. 8A and 8B illustrate one example in which a mesh network 86 dynamically updates itself when a patient support apparatus 20 exits the mesh network 86. In the example of FIG. 8A, a bed 20u is communicating data to a bed 20v via two intermediate patient support apparatuses 20; namely, a bed 20w and a stretcher 20x. The information is being transmitted through nodes 84w and 84x of these two intermediate support apparatuses 20. This data path, however, may change, such as, for example, by the movement of one or both of support apparatuses 20w and/or 20x. In the example of FIG. 8B, stretcher 20x has been moved to a new location that is outside of mesh network 86. In order for patient support apparatuses 20u and 20v to continue to communicate, a new data path is automatically created by mesh network 86. In the example of FIG. 8B, the new data path is from bed 20v to bed 20w to bed 20y to bed 20v, and/or the reverse. By dynamically changing the routing of data when one or more nodes 84 are either added or removed from mesh network 86, communication can still be accomplished without interruption.

Figure 5:
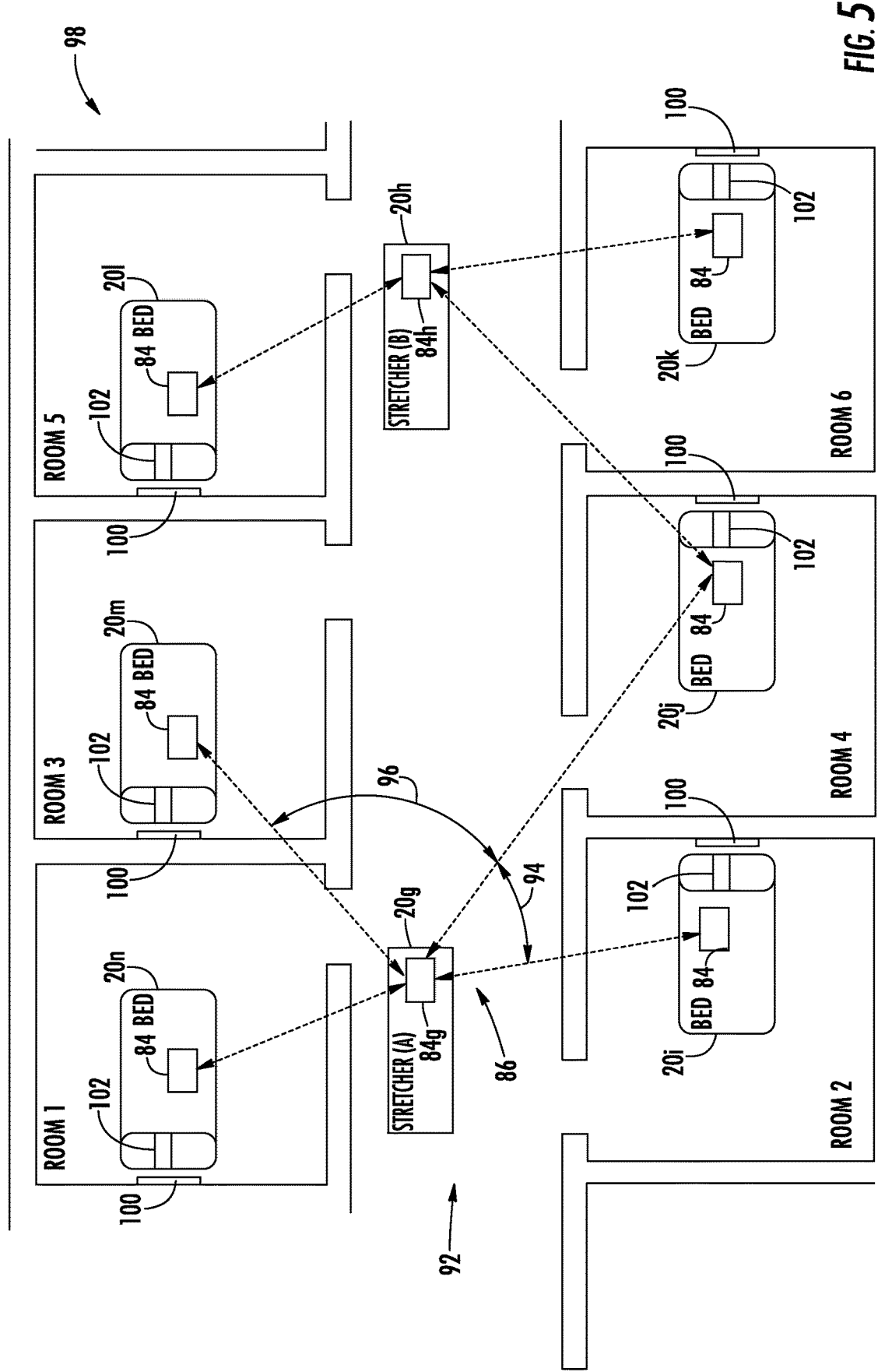
FIG. 5 is a plan view diagram of an arbitrary portion of floor plan of a healthcare facility that illustrates how some patient support apparatus embodiments of the present invention may determine their location using triangulation techniques of signals received from other patient support apparatuses.

Alternatively, or in addition to, the data transfer abilities of mesh network 86 described above, some embodiments of patient support apparatuses 20 are configured to use mesh network 86 to determine their location within a healthcare facility. This is especially useful for healthcare facilities where some apparatuses 20 are not able to determine their location at all times, such as, for example, during movement of the apparatus 20 from one location within the facility to another location within the facility. FIG. 5 illustrates one manner in which mesh network 86 is used to determine the location of one or more patient support apparatuses. Specifically, stretchers 20g and 20h are shown in a corridor or hallway 92 within an arbitrary portion of a healthcare facility 98. Stretcher 20g includes a mesh network node 84g while stretcher 20h includes a mesh network node 84h. These nodes 84g and 84h are able to wirelessly communicate with other nodes 84 that are within a vicinity of these nodes (the size of the vicinity will depend upon the specific communication protocol and/or standards used by nodes 84, as well as the communication and reception power of the electronics in nodes 84). Nodes 84g and 84h (as well as, in some cases, the nodes 84 on beds 20i, 20j, 20k, 20l, 20m, and 20n) are adapted to determine their location by using triangulation techniques, or trilateration techniques, or some combination of the two, with the other nodes 84 that are within communication range. Such triangulation techniques will enable the nodes to calculate their relative position to the other nodes that are within communication range. If one or more of the other nodes that are within communication range knows its absolute location within health care facility 98, or otherwise possesses information that enables its absolute location to be determined within facility 98, then those other nodes that know their relative location to these nodes are able to calculate their absolute position within the facility.

If configured to determine location based upon triangulation, each node 84g and 84h includes one or more antennas that are adapted to determine the direction in which signals from the other nodes 84 are received at nodes 84g and 84h, respectively. Such antennas and/or other equipment may be conventional equipment, as would be known to one of ordinary skill in the art. If a node (e.g. 84g and/or 84h) receives signals from a sufficient number of other nodes, the angular information determined from those signals will be sufficient for the node (84g or 84h) to determine its relative location to the patient support apparatuses 20 from which it received signals. This relative position can be converted into an absolute position within the healthcare facility if the absolute position of the patient support apparatuses that transmit signals to nodes 84g and/or 84h are known. In some embodiments, this conversion of relative position to absolute position is performed by one or more processors located on the patient support 20 itself, while in other embodiments, it is performed by a server or application that is running on healthcare network 70.

FIG. 5 illustrates an example of how, in one embodiment, stretcher 20g determines its location using triangulation techniques. By determining the direction from which signals are received from nodes 84 on patient support apparatuses 20i and 20j, which are in rooms 2 and 4, respectively, node 84g will be able to determine a first angle 94 (FIG. 5). By determining the direction from which signals are received from the nodes 84 on patient support apparatuses 20j and 20m, which are in rooms 4 and 3, respectively, node 84g will also be able to determine a second angle 96 (FIG. 5). Further, because the locations of beds 20i, 20j, and 20m is already known—as determined in any conventional manner, at least one of which is described in greater detail below—node 84g on patient support apparatus 20g is able to determine its absolute location within healthcare facility 98. The relative signal strength of all of the received signals may also be used in determining location.

It will be further understood by those skilled in the art that the determination of the location of a patient support apparatus 20 (such as stretcher 20g in FIG. 5) within a given facility 98 may be, in some embodiments, a determination of an approximate location. For example, the algorithms used to determine location may, in some embodiments, specify the location of the patient support apparatus merely to the level of a room or a portion of a room, or a corridor or hallway, or a section of a corridor or hallway, or some other generalized area. However, it will also be understood that finer levels of position granularity are determined in some embodiments.

If nodes 84 are equipped to determine location using trilateration or multilateration techniques, either in lieu of, or in addition to triangulation techniques, nodes 84 may be configured to determine the time it takes for signals from other nodes 84 to travel to the node whose destination is being determined. Such time of flight measurements or computations can be used to determine distances between nodes 84. This will enable a node 84 to determine its relative location. Further, if some of the absolute positions of the nodes are known, the relative position may be converted into an absolute position within the healthcare facility 98.

In one embodiment, some of the patient support apparatuses 20 are able to determine their location within a healthcare facility 98 by way of a location system that utilizes a plurality of stationary modules 100 and stationary module transceivers 102. The stationary modules 100 are positioned on walls, ceilings, or in other fixed locations whose absolute positions within the healthcare facility 98 are known. The module transceivers 102 are incorporated into some or all of the patient support apparatuses 20. In the example of FIG. 2, the electrical control system 44 of patient support apparatus 20 has transceivers 102 feeding into, and controlled by, actuator/sensor controller 50. It will be understood by those skilled in the art that transceivers 102 may be controlled by other controllers, and/or integrated into a patient support apparatus in different manners.

In one embodiment, a healthcare facility may have a plurality of patient support apparatuses 20 that are beds that include such transceivers 102, while other types of patient support apparatuses 20—such as stretchers, cots, and the like—might not include such module transceivers 102. Regardless of which specific patient support apparatuses 20 have module transceivers 102 incorporated therein, any such apparatus 20 having a module transceiver 102 incorporated therein will be able to communicate with a fixed module 100 when the apparatus is within a relatively close proximity thereto. Such proximity may be on the order of five to ten feet, or it may be other distances. In some embodiments, module transceiver 102 communicates with modules 100 via infrared signals, although it will be understood by those skilled in the art that other types of signals may be used for communication between modules 100 and transceiver 102.

In general, because the locations of modules 100 is known, and because the patient support apparatuses can only communicate with a given module 100 (via transceivers 102) then they are within a close proximity to the given module 100, the very establishment of such communication indicates that the patient support apparatus 20 is in close proximity to a given module 100 whose location is known. This allows the location of a patient support apparatus 20 to be determined.

In one embodiment, modules 100 are configured to respond to interrogations received from transceiver 102 with an identifier that uniquely identifies and distinguishes that particular module 100 from all other such modules 100 within the healthcare facility 98. The patient support apparatus 20 includes a map, table, or other information that correlates that specific module 100 to a known location, or it communicates with an application or server on network 70 that maintains such a map, table, or other information. In either case, the patient support apparatus is able to determine its location. Further details of the operation of modules 100 and transceivers 102, as well as the manner in which they can be used to determine location, are found in commonly assigned, copending U.S. patent application Ser. No. 12/573,545 filed Oct. 5, 2009 by applicants David Becker et al. and entitled LOCATION DETECTION SYSTEM FOR A PATIENT HANDLING DEVICE, the complete disclosure of which is also incorporated by reference herein.

If a location system such as the one just described (i.e. having modules 100 and transceivers 102) is used within a healthcare facility, it is customary to only position such modules 100 near locations where beds are likely to be stationed or parked (i.e. at the location in a room where the bed normally resides, or, if in a multi-bed room, at each location where the bed is normally parked). Such modules 100 are not typically placed in hallways or other locations where the beds or other patient support apparatuses are temporarily moved. The aforementioned triangulation and/or trilateration techniques used with nodes 84 may therefore be used to determine location when a patient support apparatus 20 is not within an operational vicinity of a module 100. Further, the aforementioned triangulation and/or trilateration techniques may be used with those patient support apparatuses 20 that might not be equipped with a location transceiver 102. Nodes 84 therefore complement existing location determining systems and/or fill in gaps in those existing location determining systems so that greater location knowledge—in terms of both coverage throughout the facility and/or in terms of the number of patient support apparatus—is achievable within a healthcare facility. The location information determined by way of nodes 84 is stored locally on the respective patient support apparatus 20 and/or it is forwarded to healthcare network 70 to one or more servers and/or applications running on the network 70. The forwarding of such information takes place using one or more mesh networks 86 in the manners described above, or it takes place via a direct communication with an access point 68 of network 70, or by other means.

In some embodiments, patient support apparatuses 20 that are not equipped with location transceivers 102 are, after determining their own locations, used to help determine the location or locations of other patients, or other patient support apparatuses 20 that are also not equipped with location transceivers 102, or that are equipped with such transceivers 102 but are currently located outside the vicinity of a module 100. For example, if stretcher 20g in FIG. 5 determines its location using its node 84g and one of the triangulation and/or trilateration techniques discussed above, node 84g is configured to respond to signals from node 84h of stretcher 20h that are being sent by node 84h to determine the location of stretcher 20h. In other words, node 84h of stretcher 20h is thereafter able to measure its angular relationship and/or its distance to stretcher 20g when determining its location. Thus, once a patient support apparatus 20 uses its node 84 to determine its location, it serves as a source of location information for other patient support apparatuses 20. In this way, it is possible to extend location determination abilities farther and farther away from modules 100. Or, stated alternatively, the node triangulation/trilateration position determining system described herein augments any existing location system, and may be cascaded upon itself so that patient support apparatuses that can only communicate via nodes 84 with other patient support apparatus 20 that themselves are outside the range of modules 100 can still determine their location.

The node triangulation/trilateration position determining system described herein may also be used with a position determining system that is based upon WIFI signals and the known location of the corresponding routers, access points, and/or other stationary structures that communicate those WIFI to and from the mobile patient support apparatuses 20. For example, if a patient support apparatus 20 is communicating with a specific access point 68 via second transceiver 66, that patient support apparatus 20 may be configured to determine its general location as being within a general range of the access point 68. This general range is then further refined by way of the triangulation/trilateration techniques described above. Further, this triangulation/trilateration technique is able to be used to extend the range at which patient support apparatus 20 is capable of determine its location beyond the communication range of the access point 68. Indeed, the range may be extended—depending upon the location of patient support apparatuses 20—to locations where there are no available access points 68.

The patient support apparatus to patient support apparatus communication that has so far been described can be used for two separate and potentially independent purposes. First, as was described previously, this communication may be used to create mesh networks for better routing of information between patient support apparatuses 20 and a healthcare network 70. Second, as was also just described above, this patient support apparatus to patient support apparatus communication may be used to determine location and/or to augment or complement the location determining abilities of another patient support apparatus location determining system. As will be described below with reference to FIG. 6, this patient support apparatus to patient support apparatus communication may be used for yet another purpose: transferring patient information between patient support apparatuses.

In lieu of, or in addition to, either of the mesh networking and position determining functions of nodes 84, such nodes are also useful for storing and transferring patient information, medical information, or other information between patient support apparatuses 20. That is, nodes 84 are configured to store information about the patient that is currently being support on the support apparatus 20. This information is received via transceivers 64, or by any of the other transceivers positioned on support apparatus 20. Further, the storage of this information may be in a memory within node 84, or it may be in another location on the patient support apparatus 20. Regardless of the source of the information and regardless of its storage location on the patient support apparatus, the information includes personal information and/or medical information about the patient being supported on apparatus 20. For example, the information may include the patient's name, height, weight, allergies, fall risk assessment, bed sore risk assessment, and/or any other medical or personal information that may be usefully stored on the support apparatus.

In some patient support apparatus embodiments, the stored information is displayable on an LCD screen, touchscreen, or other type of display on the patient support apparatus so that caregivers will have visual access to the information. The patient support apparatus 20 may also be configured to transmit the information locally to a pendant supported on patient support apparatus 20, or to a medical device that is plugged into, or otherwise communicatively coupled, to patient support apparatus 20. In such cases, the pendant and/or medical device are configured to display the information. In still other embodiments, the patient support apparatus wirelessly transmits the information to a portable computer device, such as a laptop, smart cell phone, personal digital assistant, or other device so that the information may be displayed thereon.

Regardless of the manner in which the patient information is displayed, or is displayable, patient support apparatus 20 is configured to transfer the patient information to another patient support apparatus 20 when the corresponding patient is transferred. In this way, the patient information follows the patient around as he or she is moved from one patient support apparatus 20 to another within healthcare facility 98. In the embodiment shown in FIG. 2, node 84 with first transceiver 64 and first transceiver controller 58 are used to control this transfer of patient information between support apparatuses 20, although it will be understood that any other transceivers could be used that enable inter-support apparatus communication.

Figure 6:
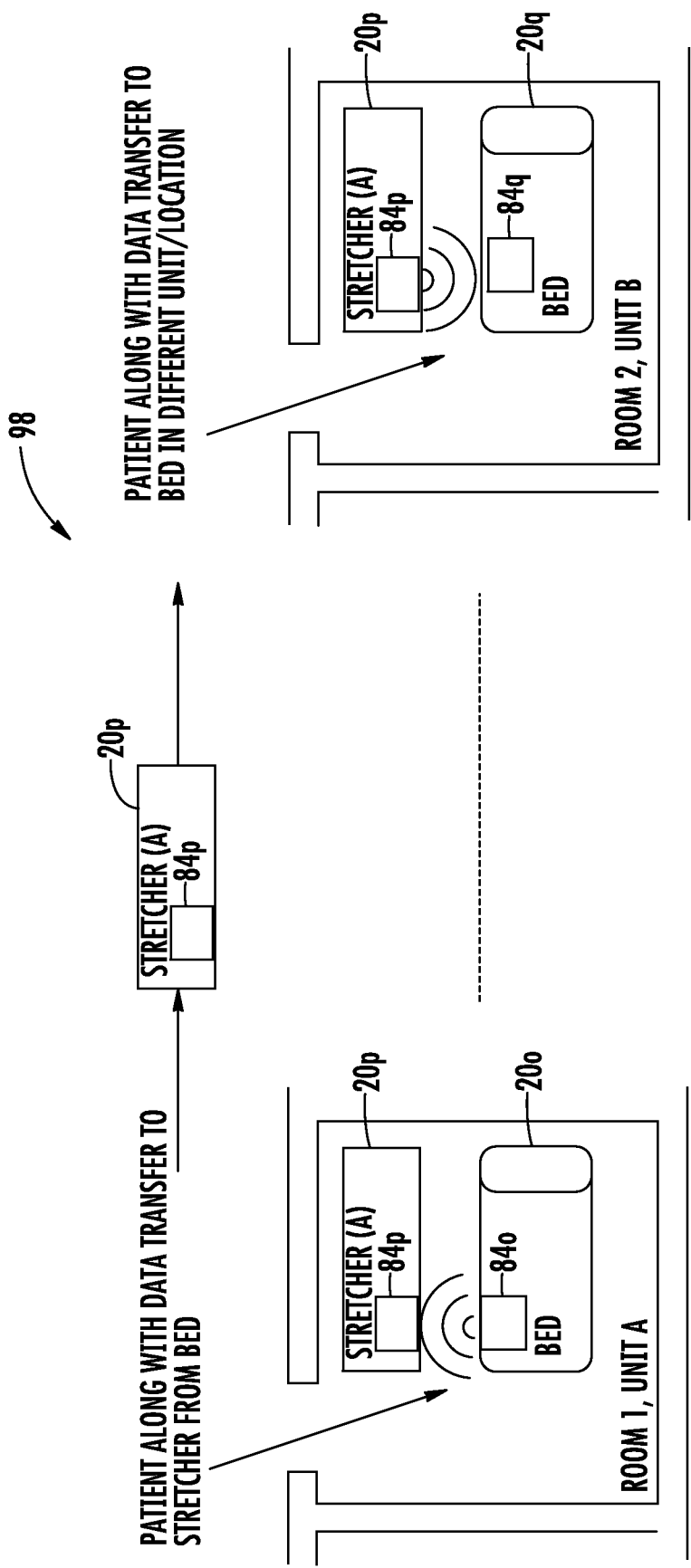
FIG. 6 is a plan view diagram of another arbitrary portion of a floor plan of a healthcare facility that illustrates how some patient support apparatus embodiments of the present invention may transfer patient information from one patient support apparatus to another as a patient is transferred from one patient support apparatus to another.

In the example of FIG. 6, a bed 20*o* is shown transferring patient data to a stretcher 20*p*. More specifically, node 84*o* of bed 20*o* is wirelessly communicating patient information to node 84*p* of stretcher 20*p*. This information transfer includes any of the information mentioned above, or any other desirably transferred information. Such information will typically be transferred when a patient (not shown) who was previously supported on bed 20*o* is transferred to stretcher 20*p*. Once the patient and his or her corresponding patient information have been transferred to stretcher 20*p*, stretcher 20*p* may be transported to another location, such as, for example, a room labeled "Room 2, Unit B" in FIG. 6. At the second location, the patient may, in some cases, be transferred to yet another patient support apparatus 20. In the example of FIG. 6, the patient may be transferred off of stretcher 20*p* and onto a different bed 20*q*. When this patient transfer occurs, the stretcher 20*p* will also transfer the corresponding patient data to bed 20*q* as well. In this manner, bed 20*q* will be in possession of the information that corresponds to the patient that has just been transferred thereto. Such apparatus-to-apparatus 20 transfers enable patient information to be portable and to easily accompany a patient as he or she is moved throughout a healthcare facility.

In some embodiments, the transfer of patient information from a first patient support apparatus 20 to a nearby second patient support apparatus 20 is commenced in response to an authorized individual, such as a caregiver, physically activating a data transfer mechanism on one or both of the patient support apparatuses. The mechanism is implemented as a touchscreen in one embodiment, although it will be understood that it may alternatively include one or more buttons, additional touchscreens, one or more switches, levers, or other physical components. Such mechanisms may be part of any of any of the user controls on patient support apparatus, or it may be positioned elsewhere. In the example of FIG. 2, patient support apparatus 20 includes a first set of user controls 104*a* located on a first siderail, a second set of user controls 104*b* located on a second siderail, and a third set of user controls 104*c* located on a footboard of patient support apparatus 20. The mechanism for transferring data between support apparatuses 20 is positioned the third set of user controls 104*c*, although it could be positioned on any one or more of these user controls 104.

In some embodiments, the transfer of patient data is automatically commenced when patient support apparatus 20 senses that a patient has exited and when another patient support apparatus 20 is detected to be within close communication distance (such as via a measurement of signal strength between nodes 84). The detection of a patient exiting a support apparatus 20 may be implemented by a conventional bed exit detection system 106, such as, but not limited to, one of the type illustrated in FIG. 2, which includes a plurality of load cells 108 that feed force data into a scale system controller 52. The force data measurements represent the forces exerted by the patient onto the patient support deck 30, and their absence and/or diminishment beyond a threshold indicate that the patient is off of deck 30.

A patient support apparatus 20 may also be configured to receive patient information from another support apparatus 20, or from another source, upon the manipulation of one or more user controls 104, or it may take place automatically. When configured to take place automatically, the node 84 of the receiving support apparatus 20 monitors its bed exit detection system, or scale system, to determine if there have been any recent increases in weight (signifying the addition of a patient to a previously unoccupied patient support deck 30). If there have, and if node 84 of the receiving support apparatus is detecting a nearby node 84 that is transferring patient data, the node 84 of the receiving support apparatus 20 stores the incoming patient data and accepts it as corresponding to the recently added patient. If the receiving patient support apparatus has patient data stored therein from a prior patient, this may be automatically overwritten by the new data, or the old data may be stored therein for future user or future retrieval.

A verification process is incorporated into the patient data transfer such that a caregiver may easily determine whether the patient data has been transferred correctly. In some embodiments, a graphic or textual display on the receiving support apparatus 20 will display the received name of the patient and prompt the caregiver to confirm that this corresponds to the patient now positioned thereon. If it does not, then the support apparatus 20 discards or ignores the new patient data, or otherwise concludes that it does not correspond to the patient currently occupying that patient support apparatus. Once the data has been verified by the caregiver as having been properly transferred, the receiving support apparatus 20 sends a signal back to the transmitting apparatus indicating it is OK to purge, overwrite, or no longer save, the patient data that it just transferred. In this way, the now empty patient support apparatus will have its memory effectively empty so that it is able to receive patient data corresponding to the next patient. In some embodiments, a patient support apparatus 20 may retain the patient data after transferring it to another support apparatus so that it may be retrieved for potential further use.

In addition to patient data, the transferred data may also include information about the usage of patient support apparatus, such as the amount of time the patient support apparatus was used by a particular patient, and/or any other information that may be useful for billing purposes. Still further, as will be described in greater detail below, the transferred information may include information gathered by one or more medical devices that were used or associated with the patient, including not only medical information that may be useful for treating or caring for the patient, but also usage information that may be useful for billing purposes.

The automatic transfer of information to an adjacent patient support apparatus may also be configured to be implemented based upon an radio frequency (RF) tag, bracelet, or other structure worn by a patient that may be detected automatically by one or more sensors positioned on each of the patient support apparatuses. When a support apparatus 20 detects a new patient has entered it via such a tag, bracelet, or other device, it requests via one or more node 84 transmissions that the adjacent patient support apparatus transfer the corresponding patient information, or other information, to it.

FIG. 7 illustrates yet another use for nodes 84 in one or more patient support apparatuses. Specifically, FIG. 7 illustrates how nodes 84 are useful for communicating medical information received from one or more medical devices 110. The use of nodes 84 in patient support apparatuses 20 to communicate medical information may be the sole use of nodes 84 in a given patient support apparatus, or it may be combined with any of the aforementioned use of nodes 84 in patient support apparatuses 20 (e.g. mesh network communication, location determination, and patient information storage and transfer).

In the arbitrary example illustrated in FIG. 7, a patient 112 is shown positioned on a bed 20*r* having associated therewith two medical devices 110*a* and 110*b*. Medical devices 110*a* and 110*b* are configured to communicate with node 84*r* of bed 20*r*. Medical devices 110*a* and 110*b* therefore are able to transfer data gathered by the medical devices 110*a* and 110*b* to bed 20*r*, which either uses some or all of the transferred information itself, or it forwards it on for communication to healthcare network 70. Patient support apparatus 20*s* similarly has two medical devices 110 associated with it—devices 110*c* and 110*d*—which communicate information to node 84*s* on bed 20*s*. A third bed 20*t* is shown with no medical devices associated with it, yet it may still be in communication via its associated node 84*t* with node 84*r* and/or node 84*s*.

As was alluded to above, each patient support apparatus 20 in some embodiments includes a sensor for automatically detecting a patient ID device 114 that is worn, or otherwise carried with, each patient. The patient ID device 114 carries sufficient information for one or more sensors on patient support apparatus 20 to automatically determine the identity of a patient positioned thereon. With this patient information, support apparatus 20 is able to associate the data received from the one or more medical devices 110 that are communicating data to support apparatus 20 so that the medical data is correlated to a specific patient. The patient support apparatus 20 then forwards this medical data, with the corresponding patient identification, to network 70, which includes one or more applications or servers that utilize this data. Such servers or applications may include an electronic medical records system, or other system.

When forwarding this data to network 70, the nodes 84 of the respective support apparatuses 20 may forward the information thereto by first transmitting the information to one or more intermediate patient support apparatuses before the data ultimately arrives at network 70. This may involve routing the data through a mesh network, as described previously, or it may be forwarded in other manners. As shown in FIG. 7, beds 20*s* and 20*t* both forward data to access point 68, and receive data from access point 68, by routing the data through bed 20*r*. Bed 20*r*, on the other hand, may communicate directly with access point 68 via second transceiver 66.

Figure 9:
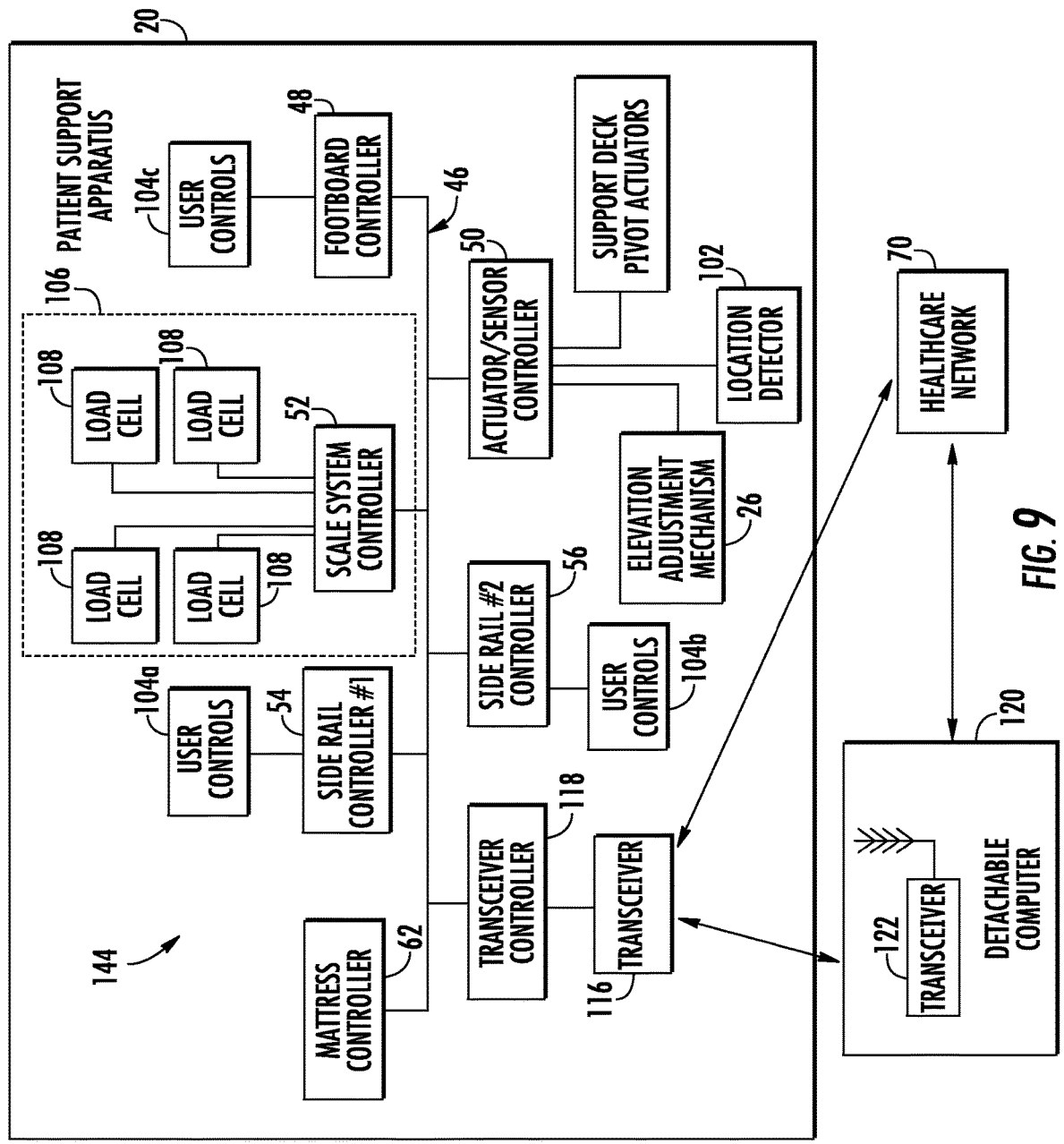
FIG. 9 is a diagram of an alternative electrical control system that may be used with any of the patient support apparatuses described herein.

FIG. 9 illustrates an alternative electrical control system 144 that may be used on any one or more of the patient support apparatuses 20 described herein. Electrical control system 144 includes multiple components that are common to electrical control system 44 described above (FIG. 2). Those components in common are labeled with the same reference numbers, and operate in the same manners described above. Further description of those components is therefore not provided.

Electrical control system 144 differs from the previously described control system 44 in that first and second transceivers 64 and 66, respectively, have been eliminated. A local transceiver 116 has also been added, along with a local transceiver controller 118. Local transceiver 116 is adapted to communicate with a detachable computer 120 that is physically supportable on patient support apparatus 20. More specifically, local transceiver 116 communicates via Bluetooth, Zigbee, or any other suitable wireless protocol with a computer transceiver 122 incorporated into detachable computer 120. Detachable computer 120 is a conventional a laptop, a tablet computer (such as, but not limited to, an iPad), or any other portable computer that may be removably coupled to patient support apparatus 20. The removable coupling of the computer 120 to patient support apparatus 20 may involve only a physical coupling in which the computer is physically supported and/or secured to patient support apparatus 20, but communication takes place wirelessly. Alternatively, the coupling may involve one or more wires, such as communication wires, that are connected between the computer 120 and patient support apparatus 20. In either case, the computer 120 is able to communicate with transceiver 116 such that information may be sent from computer 120 to patient support apparatus 20, and/or information may be received from patient support apparatus 20 by computer 120. Such information includes any of the information discussed above in any of the embodiments described herein such as, but not including, patient information, medical information, bed status information, relayed information received from other support apparatuses 20, information to be relayed to other patient support apparatuses 20, location information, etc.

The coupling of computer 120 to patient support apparatus, in some embodiments, enables the computer 120 to function as a user interface in which any or all functions of the patient support apparatus 20 are able to be controlled by computer 120. In one embodiment, when computer 120 is coupled to patient support apparatus 20, a touch screen on computer 120 appears that includes icons and/or graphics that mimic a control panel already on patient support apparatus 20, or that mimics a control panel that is of the type that might be on patient support apparatus 20, thereby giving the caregiver the means for controlling patient support apparatus 20 through computer 120. One example of a removable computer that may be coupled to a patient support apparatus 20 is described in greater detail in commonly assigned, copending U.S. provisional patent application Ser. No. 13/783,699, filed Mar. 4, 2013 by applicants Cory Herbst et al. and entitled PATIENT SUPPORT, the complete disclosure of which is hereby incorporated herein by reference. Any or all of the other features described in this application may also be incorporated into any of the patient support apparatuses 20 described herein.

FIG. 10 illustrates an arbitrary portion of a healthcare facility 98 in which multiple patient support apparatuses 20 are shown incorporating multiple of the concepts described herein. These include the use of nodes 84 for determining location, for creating a mesh network, for transferring patient information, and for relaying medical device information. For example, patient support apparatus 20c receives information from medical devices D1 and D2, which it then relays onto patient support apparatus 20a via direct communication between nodes 84c and 84a. When patient support apparatus 20a receives this information, it passes it onto network 70 via transceiver 66. Alternatively, if the connection between patient support apparatus 20a and network 70 is not operable, or otherwise not suitable, patient support apparatus 20a is able to relay this information to another support apparatus 20 that then forwards this information to network 70.

Also shown in FIG. 10 is the transfer of patient information from support apparatus 20a to support apparatus 20z, which then moves down one or more hallways to a different room, where it then transfers to the patient information to support apparatus 20b. This patient information is transferred via nodes 84 in any of the manners described above. While stretcher 20z is in transit, it may determine its location using nodes 84 by any of the triangulation, trilateration, or multilateration methods described herein, or in other manners. Any information on any of the servers or applications on network 70 may also be transmitted to the desired patient support apparatus in a reverse manner.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various alterations and changes can be made to any of the foregoing embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
   a base;
   a frame supported by the base;
   a patient support deck supported by the frame, the patient support deck adapted to provide support for a patient;
   a control system adapted to control a feature of the patient support apparatus; and
   a wireless transceiver adapted to wirelessly receive signals from another patient support apparatus, the signals including location information that indicates a location of the another patient support apparatus within a healthcare facility; wherein the control system is adapted to use the location information, along with a measurement of a strength of the signals, to estimate a location of the patient support apparatus within the healthcare facility.

2. The patient support apparatus of claim 1 wherein the wireless transceiver is adapted to wirelessly receive signals from a plurality of patient support apparatuses, the signals including location information that indicates a location of each of the plurality of patient support apparatuses within the healthcare facility; wherein the control system is adapted to use the location information of each of the plurality of patient support apparatuses, along with a measurement of a strength of each of the signals, to estimate a location of the patient support apparatus within the healthcare facility.

3. The patient support apparatus of claim 1 wherein the control system is further adapted to transmit the estimate of the location of the patient support apparatus to a recipient using the wireless transceiver.

4. The patient support apparatus of claim 3 wherein the control system is further adapted to transmit the estimate of the location of the patient support apparatus to a healthcare network using a different wireless transceiver positioned on the patient support apparatus.

5. The patient support apparatus of claim 1 further including an electronic memory adapted to store patient information about a patient positioned on the patient support deck;
wherein the control system is further adapted to wirelessly transmit the patient information from the electronic memory to a different patient support apparatus when the patient is transferred from the patient support apparatus to the different patient support apparatus.

6. The patient support apparatus of claim 5 further including:
a user control in communication with the control system, the user control adapted to control when the wireless transceiver transmits the patient information to the different patient support apparatus;
a display that displays an identifier of the different patient support apparatus to which the patient information is wirelessly transmitted; and
wherein the patient information includes a patient identifier.

7. The patient support apparatus of claim 1 wherein the control system is adapted to be able to wirelessly receive information via the wireless transceiver from a different patient support apparatus about a feature of the different patient support apparatus, and the control system is adapted to be able to forward the information from the different patient support apparatus off of the patient support apparatus via the wireless transceiver.

8. The patient support apparatus of claim 7 wherein the information from a different patient support apparatus about a feature of the different patient support apparatus includes information related to one or more of the following: a bed exit condition of the different patient support apparatus, a siderail condition of the different patient support apparatus, a height of the different patient support apparatus, a brake status of the different patient support apparatus, and an angular orientation of a component of the different patient support apparatus.

9. The patient support apparatus of claim 1 wherein the wireless transceiver is further adapted to receive medical device data from a medical device, and the control system is adapted to be able to forward the medical device data off of the patient support apparatus via the wireless transceiver.

10. The patient support apparatus of claim 9 wherein the control system is further adapted to be able to forward the medical device data off of the patient support apparatus via a different transceiver, and the control system chooses between the wireless transceiver and the different transceiver for forwarding the medical device data off of the patient support apparatus.

11. The patient support apparatus of claim 9 wherein the medical device is one of a ventilator, a vital signs monitor, a respirator, an infusion pump, an IV pump, a temperature sensor, and a blood oxygen saturation monitor.

12. The patient support apparatus of claim 1 wherein the patient support apparatus is one of a cot, a stretcher, a bed, and a recliner.

13. The patient support apparatus of claim 1 further including a second wireless transceiver in communication with the control system, the control system adapted to be able to forward the estimate of location of the patient support apparatus off of the patient support apparatus via the second wireless transceiver.

14. The patient support apparatus of claim 13 wherein the control system selects a recipient of the estimate of location based upon data received from a plurality of potential recipients wherein the data includes information about the communication capabilities of the potential recipients with a healthcare Ethernet.

* * * * *